(12) United States Patent
Mevel et al.

(10) Patent No.: US 11,278,631 B2
(45) Date of Patent: Mar. 22, 2022

(54) RAAV WITH CHEMICALLY MODIFIED CAPSID

(71) Applicants: CENTRE NATIONAL DE LA RECHERCHE SCIENTIFIQUE (CNRS), Paris (FR); INSTITUT NATIONAL DE LA SANTE ET DE LA RECHERCHE MEDICALE (INSERM), Paris (FR); UNIVERSITE DE NANTES, Nantes (FR); CENTRE HOSPITALIER UNIVERSITAIRE DE NANTES, Nantes (FR)

(72) Inventors: Mathieu Mevel, Nantes (FR); David Deniaud, Nantes (FR); Eduard Ayuso, Nantes (FR)

(73) Assignees: CENTRE NATIONAL DE LA RECHERCHE SCIENTIFIQUE (CNRS), Paris (FR); INSTITUT NATIONAL DE LA SANTE ET DE LA RECHERCHE MEDICALE (INSERM), Paris (FR); UNIVERSITE DE NANTES, Nantes (FR); CENTRE HOSPITALIER UNIVERSITAIRE DE NANTES, Nantes (FR)

( * ) Notice: Subject to any disclaimer, the term of this patent is extended or adjusted under 35 U.S.C. 154(b) by 0 days.

(21) Appl. No.: 17/172,581

(22) Filed: Feb. 10, 2021

(65) Prior Publication Data
US 2021/0205467 A1 Jul. 8, 2021

Related U.S. Application Data

(63) Continuation of application No. 16/308,740, filed as application No. PCT/EP2017/064089 on Jun. 9, 2017.

(30) Foreign Application Priority Data

Jun. 9, 2016 (EP) .................................... 16305681

(51) Int. Cl.
*A61K 47/69* (2017.01)
*A61K 48/00* (2006.01)
*A61K 49/18* (2006.01)
*C12N 7/00* (2006.01)

(52) U.S. Cl.
CPC ...... *A61K 47/6901* (2017.08); *A61K 48/0091* (2013.01); *A61K 49/1896* (2013.01); *C12N 7/00* (2013.01); *C12N 2750/14121* (2013.01); *C12N 2750/14122* (2013.01); *C12N 2750/14133* (2013.01); *C12N 2750/14134* (2013.01); *C12N 2750/14142* (2013.01); *C12N 2750/14143* (2013.01)

(58) Field of Classification Search
CPC ................................................ A61K 47/6901
See application file for complete search history.

(56) References Cited

U.S. PATENT DOCUMENTS

2016/0369298 A1 12/2016 Marsic et al.

FOREIGN PATENT DOCUMENTS

| WO | WO 00/02654 A1 | 1/2000 |
| WO | WO 2005/106046 A1 | 11/2005 |
| WO | WO 2015/048534 A1 | 4/2015 |
| WO | WO 201 5/062516 A1 | 5/2015 |

OTHER PUBLICATIONS

Huang et al. (2021, Life Sciences, vol. 270, pp. 1-7) (Year: 2021).*
Choudhury et al., (2016, Molecular Therapy, vol. 24(4), pp. 726-735) (Year: 2016).*
Hudry et al. (2019, Neuron, vol. 101, pp. 839-862) (Year: 2019).*
Mevel et al., 2020, Chem Sci., vol. 11, pp. 1122-1131 (Year: 2020).*
International Search Report dated Sep. 20, 2017 in PCT/EP2017/064089 filed Jun. 9, 2017, citing documents AA, AM,AN, AV and AW therein, 5 pages.
Kye-Il Joo, et al., "Enhanced Real-Time Monitoring of Adeno-Associated Virus Trafficking by Virus-Quantum Dot Conjugates" ACS Nano, vol. 5, No. 5, XP055327681, May 24, 2011, 22 pages.
Christiane E. Wobus, et al., "Monoclonal Antibodies against the Adeno-Associated Virus Type 2 (AAV-2) Capsid: Epitope Mapping and Identification of Capsid Domains Involved in AAV-2-Cell Interaction and Neutralization of AAV-2 Infection" Journal of Virology, XP055233477, vol. 74, No. 19, Oct. 1, 2000, pp. 9281-9293.
Eric D. Horowitz, et al. "Glycated AAV Vectors: Chemical Redirection of Viral Tissue Tropism" Bioconjugate Chemistry, 2011, pp. 529-532.

\* cited by examiner

*Primary Examiner* — Thaian N. Ton
*Assistant Examiner* — David A Montanari
(74) *Attorney, Agent, or Firm* — Oblon, McClelland, Maier & Neustadt, L.L.P.

(57) ABSTRACT

The invention is directed to the field of gene therapy, i.e. gene delivery into target cells, tissue, organ and organism, and more particularly to gene delivery via viral vectors. The inventors showed that it is possible by chemical coupling to modulate the coupling of a ligand in the surface of the capsid of AAV, for example AAV2 and AAV3b. In particular, the present invention relates to a recombinant Adeno-Associated Virus (rAAV) vector particle having at least one primary amino group contained in the capsid proteins, chemically coupled with at least one ligand L, wherein coupling of said ligand L is implemented through a bond comprising a —CSNH— bond and an optionally substituted aromatic moiety.
Particularly, the inventors tested the chemical coupling of mannose ligand on AAV2 for subretinally injection to rats. The present invention further relates to a method for chemically coupling an Adeno-Associated Virus (AAV) vector particle with at least one ligand L and to a Recombinant Adeno-Associated Virus (rAAV) vector particle obtained by said method as well as a pharmaceutical composition comprising it and their corresponding medical use.

9 Claims, 13 Drawing Sheets
Specification includes a Sequence Listing.

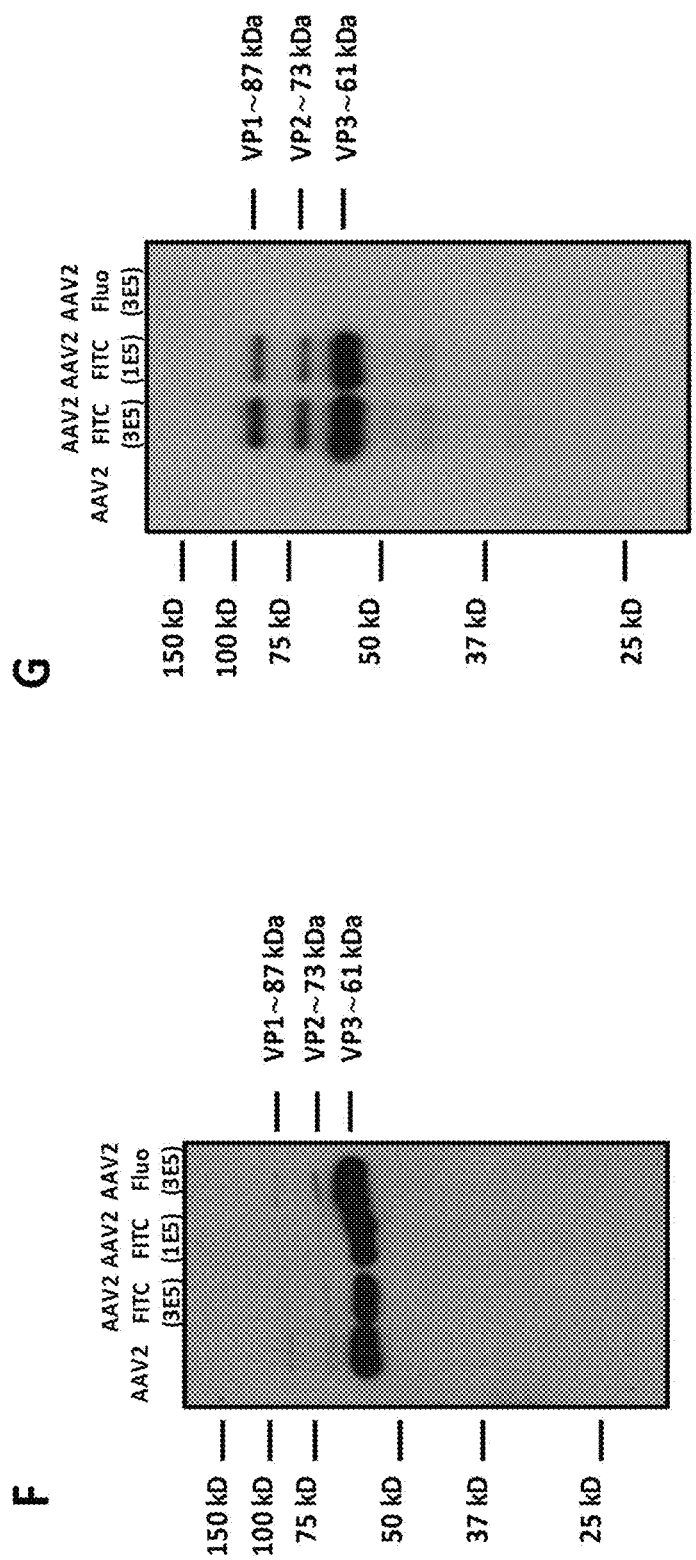
Figure 1 (continuation)

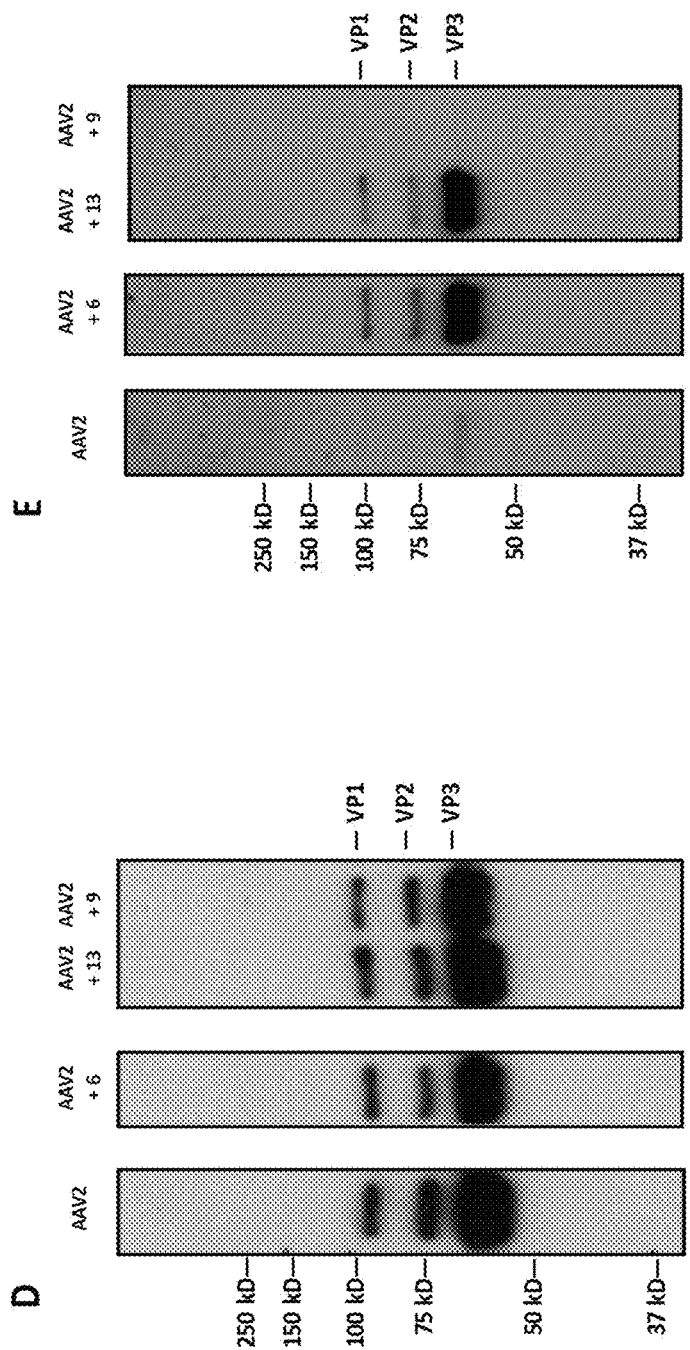
Figure 3 (continuation)

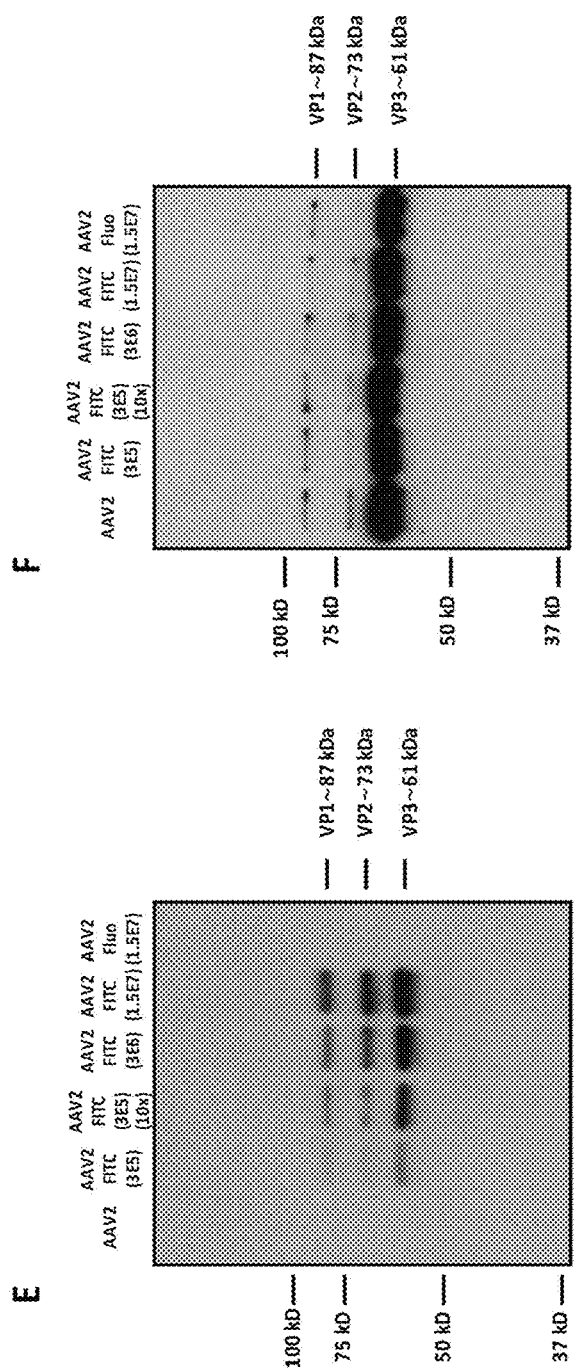
Figure 5 (Continuation)

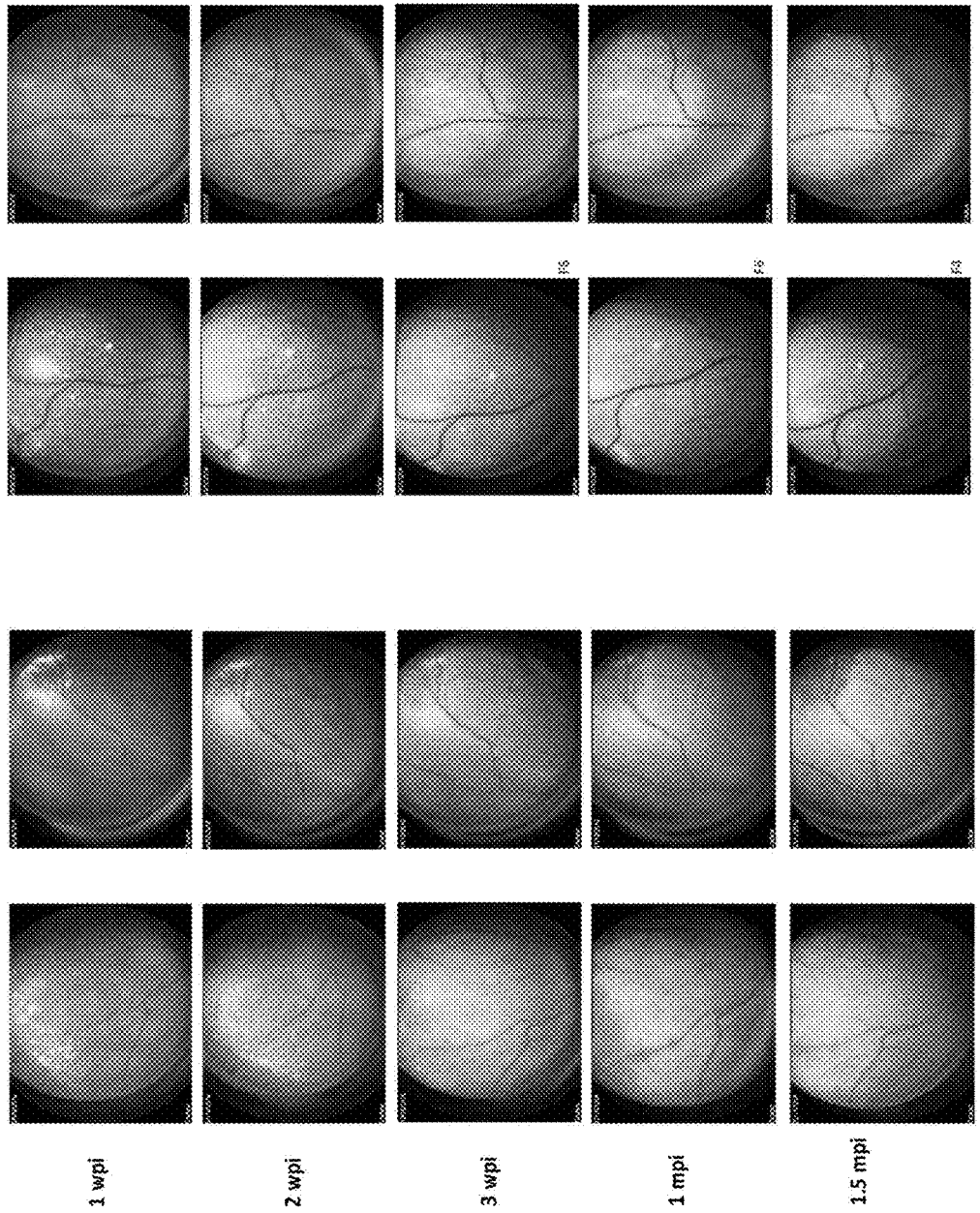
Figure 7 (continuation)

RAAV WITH CHEMICALLY MODIFIED CAPSID

The present invention generally relates to the field of gene therapy, i.e. gene delivery into target cells, tissue, organ and organism, and more particularly to gene delivery via viral vectors.

The present invention is more particularly dedicated to recombinant Adeno-Associated Virus (rAAV) vector particles, chemically coupled on their capsid with at least one ligand and to a method for producing said recombinant Adeno-Associated Virus (rAAV) vector particle. Furthermore, the present invention relates to the use of these recombinant Adeno-Associated Virus (rAAV) vector particles as a therapeutic and/or diagnostic means.

BACKGROUND OF THE INVENTION

Gene therapy is more particularly considered in the present invention. Although gene therapy was originally developed to correct defective genes that underlie genetic diseases, today gene therapy can be used to treat a broad range of disorders including acquired diseases such as cancer, heart stroke or metabolic disorders. A common approach to address this issue involves the delivery of nucleic acids to the nucleus. These nucleic acids may then be inserted into the genome of the targeted cell or may remain episomal. Delivery of a therapeutic nucleic acid to a subject's target cells can be carried out via numerous methods, including the use of viral vectors. Among the many viral vectors available (e.g, retrovirus, lentivirus, adenovirus, and the like), adeno-associated virus (AAV) is gaining popularity as a versatile vector in gene therapy, particularly for in vivo applications.

Adeno-associated virus (AAV) is a member of the parvoviridae family. The AAV genome is composed of a linear single-stranded DNA molecule which contains approximately 4.7 kilobases (kb) and consists of two major open reading frames encoding the non-structural Rep (replication) and structural Cap (capsid) proteins.

Recombinant vectors derived from AAV are now becoming therapeutic products, and recently one of them has received market approval for the treatment of a rare genetic disease (lipoprotein lipase deficiency).

Viral vectors derived from adeno-associated viruses (AAV) have indeed become the tool of choice for in vivo gene transfer, mainly because of their superior efficiency in vivo, compared to other vectors, their tropism for a broad variety of tissues, and their excellent safety profile. Therapeutic efficacy following AAV vector gene transfer was documented in several preclinical studies and, over the past decade, some of these results were successfully translated to the clinic, leading to some of the most exciting results in the field of gene therapy. The recent market approval of the first AAV-based gene therapy product in Europe constitutes additional evidence that the field is progressing from proof-of-concept studies toward clinical development.

However, most clinical trials using AAV as vehicle for transgenes showed its critical limitations: (i) its reduced therapeutic index (i.e. high doses of vectors are usually required to achieve therapeutic efficacy); (ii) its broad biodistribution; (iii) and its poor efficacy in the presence of pre-existing neutralizing antibodies.

One limitation of AAV lies indeed in their broad tropism, which results in transgene expression in other tissues other than those where transgene expression is desired. It is also well recognized that host and vector-related immune challenges need to be overcome for long-term gene transfer.

Most of the gene therapy applications to date have used the serotype 2 (AAV2). Transduction of a wide range of post-mitotic cells in vivo such as muscle cells, hepatocytes or neurons in mammals partly explains its popularity. This serotype has also been used for gene transfer to the muscle and liver in clinical trials for Hemophilia B and the retina for treating Leber Congenital Amaurosis.

However there are still complications and limitations with the use of this vector. First, high doses of the vector are usually required since transduction efficacy in vivo is generally low, resulting in increased toxicity. One of the most important complication is due to the fact that 50-90% of the human population is seropositive for AAV2 and has developed neutralizing antibodies (NAb) against AAV2 that impair gene delivery. The discovery of naturally occurring AAV isolates (from 1 to 12) in humans and animals species and the genetic modification of the capsid of these AAV serotypes using molecular tools resulted in promising results in preclinical animals models and phase I/II clinical trials, which foster exciting clinical translation in the near future. However their therapeutic index remains low, which implies that high concentration of them still needs to be administered with concomitant adverse effects. At the same time, manufacturing clinical lots of AAV vectors has considerably progressed in the past decade and large scale manufacturing methods are now available for the preindustrial pharmaceutical stage in which gene therapy is entering. Nonetheless, if high doses of vectors are required for phase III and commercialization current methods will not be able to support such demand.

As said strategies, which have indeed demonstrated the potential of novel AAV serotypes (and related genetic variants), were not considered satisfying as not achieving precise tropism, enabling the selective transduction of a target cell type, further efforts to increase tropisms of AAV-derived vectors are currently underway. Indeed to counterbalance the lack of specificity of the AAV-derived vectors, extremely large amounts of AAV-derived vectors need to be administered to reach a therapeutic threshold, which is not desired for safety concerns as well as manufacturing limitations.

Various attempts have been pursued for this purpose, such as genetic introduction of peptide epitopes with targeting specificities into the viral surface. Further strategies were using linker molecules with two specificities, such as bispecific antibodies, one specificity being directed to the viral capsid, the other to the receptor, were introducing adaptor domains (Z domain of protein A, biotin) for non covalent attachment of protein ligands.

For example in document WO00/002654, the altered tropism is made primarily for preventing the binding of the AAV to virus receptors of the original target cell. In a particular embodiment, the increased affinity vis-a-vis the target cell is also referred in this document. Still in this document, antibody fragments are linked to the capsid. According to an alternative embodiment, the other end of the antibody can be coupled to ligands to improve the affinity vis-a-vis the target (preparation of "diabodies").

Combined biological and chemical coupling on the AAV capsid has also been proposed in the past for improving the selectivity of AAV-derived vectors to the target tissue.

For example WO2005/106046 proposes a method combining genetic modification and chemical modification of the capsid. The chemical modification that is the second stage of the process relies on the presence of residues cysteines whose capsid was enriched by genetic pathway in a first step. AAV particles may thus be grafted with ligands, polymers, gold nanoparticles, fluorescents molecules, magnetic or substances biochemically active substances. However, the coupling is performed via disulfide, thioester and/or thioether bonds and via NCS bonds as in the present invention as detailed herein after.

The article E. D. Horowitz et al "Glycated AAV Vectors: Chemical Redirection of Viral Tissue Tropism" Bioconjugate Chemistry, 2011, 22, 529-532 describes the problem of cell tropism among other technical problems. In particular, generation of unnatural amino acid side chains through capsid glycation serves as an orthogonal strategy to engineer AAV vectors displaying novel tissue tropisms for gene therapy applications.

In WO2015/062516, a non-natural amino acid, such as an amino acid comprising an azido, is inserted into the capsid by genetic modification prior to a coupling step by chemical-click to change the capsid of AAV and its tropism for the target cell.

One may also cite another dimension of the research in the field of AAV as a vehicle for gene therapy, i.e. coating of viral particles with polymers such as polyethylene glycol (PEG) or poly-(N-hydroxypropyl)methacylamide (pHPMA) with the aim of reducing specific and unspecific interactions with nontarget tissues.

However said approaches are still not entirely satisfying as various steps are mostly involved before achieving the AAV-derived vectors. Also, to incorporate specific ligands these approaches required the genetic modification of the capsid. In other words, the existing processes for incorporating ligands into the AAV capsid surfaces do not offer the desired flexibility and simplicity, since it cannot be applied to a wild type capsid. It has to be noted that the introduction of a genetic modification in the capsid can change the tropism of the vector and can modify the production yield and other biological parameters. In addition, this genetic modification has to be performed for each new serotype that needs to be modified. In summary, no universal method exists to couple a desired target ligand to the AAV capsid.

It is also known from Kye-Il Joo et al "Enhanced Real-Time Monitoring of Adeno-Associated Virus Trafficking by Virus-Quantum Dot Conjugates", ACS NANO, vol. 5, no. 5, 24 May 2011 a chemical reaction for coupling quantum dots (QDs) in the capsids o AAV particles. However, a carbodiimide coupling is implemented and not a thiourea bond as in the present invention as it will be apparent from the following description.

At last, C. E. Wobus et al "Monoclonal Antibodies against the Adeno-Associated Virus Type 2 (AAV-2) Capsid: Epitope Mapping and Identification of Capsid Domains Involved in AAv-2 Cell Interaction and Neutralization of AAV-2 Infection", Journal of Virology, vol. 74, no. 19, 1 Oct. 2000, pages 9281-9293 describes the labelling of empty capsids with FITC. However, as it will be described in detail herein after, only genome containing capsids are concerned in the present invention and coupled to ligand L through a bond comprising a —CSNH— and an aromatic moiety.

Therefore, there exists a need for finding a method to modify AAV-derived vectors by chemical coupling, for increasing their ability to target a specific organ or tissue, in particular by an in vivo gene delivery.

There is also a need to modify the AAV-derived vectors without requiring a step of modification of the AAV amino acid capsid sequence.

Furthermore, there is a need for new surface-modified AAV-derived vectors with improved virus-mediated gene transfer into specific cell types.

More generally, there exists a need for new methods for chemically coupling ligands of any nature on AAV-derived vectors capsids surface, i.e. a variety of chemical moieties, for example to improve the "specific activity" and/or "the therapeutic index".

More particularly, there is a need to provide new means for modifying the particle capsids with moieties such as synthetic polymers, peptides, carbohydrates or lipids.

It further exists a need to find out chemically-modified Recombinant Adeno-Associated Virus (rAAV) vector particle allowing decreasing the therapeutic dose.

The present invention precisely aims to provide a novel recombinant Adeno-Associated Virus (rAAV) vector particle complying with the previous requirements, its producing method and its therapeutic and/or diagnostic uses.

SUMMARY OF THE INVENTION

Therefore, according to one of its aspects, the invention is directed to a recombinant Adeno-Associated Virus (rAAV) vector particle having at least one primary amino group contained in the capsid proteins, chemically coupled with at least one ligand L, wherein said ligand L is implemented under the form of a compound of formula (I)

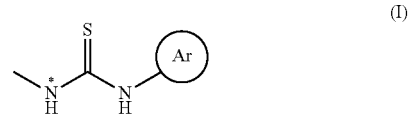

whith
N* being the nitrogen atom of one primary amino group contained in the capsid proteins and,

representing an optionally substituted arylene or a heteroarylene radical, directly or not, covalently bound to at least one ligand L.

According to another of its aspects, the invention relates to a method for chemically coupling an Adeno-Associated Virus (AAV) vector particle with at least one ligand L, said method comprising at least the steps of:
having an Adeno-Associated Virus (AAV) particle having at least one primary amino group contained in the capsid proteins, and
contacting said AAV particle with a reagent of formula (II)

wherein B is
a radical (L)m(X)Ar—
with
L being as defined herein after,
m representing an integer from 1 to 1000,
Ar representing an arylene or heteroarylene radical, and is more particularly as defined herein after, and
X representing a bond or a spacer between said ligand(s) L and Ar, in conditions suitable for reacting the primary amino group with the —N=C=S moiety of the reagent of formula (II).

The invention further relates to a Recombinant Adeno-Associated Virus (rAAV) vector particle obtained by said method conform to the present invention.

In still another aspect, the present invention is directed to the Recombinant Adeno-Associated Virus (rAAV) vector particle according to the present invention, for use as a medicament, in particular for delivering therapeutic nucleic acids (genes, RNA, miRNA, lncRNAs, ... ) or for inducing a corrective genome editing; as a prophylactic means; as a diagnostic means, such as an imaging agent or for use for efficiency studies for gene therapy.

The invention also relates to a pharmaceutical composition comprising the Recombinant Adeno-Associated Virus (rAAV) vector particle of the invention in a pharmaceutically acceptable carrier.

The chemical modification considered in the framework of the present invention may therefore be carried out by formation of a covalent bond directly to the amino groups present on the AAV capsid without requirements of previous genetic modifications to the capsid sequence.

The major advantage of chemical coupling, as opposed to the generation of engineered AAV strains using molecular genetic tools, is the possibility to modify the particle capsids with moieties such as synthetic polymers, peptides, carbohydrates or even lipids that cannot be incorporated genetically. Also, new genetic variants of AAV capsid might be problematic to produce and characterize for their use in clinical trials since these synthetic capsids have to be studied at various levels, including tropism, biodistribution, vector assembly, production yields and purification strategies.

Other aspects and advantages of the invention will be apparent from the following detailed description of the invention, and in particular in connection to the variety of organic entities that can functionalize the capsids, such as small molecules, polymers or peptides.

DETAILED DESCRIPTION OF THE INVENTION

Figure 1:
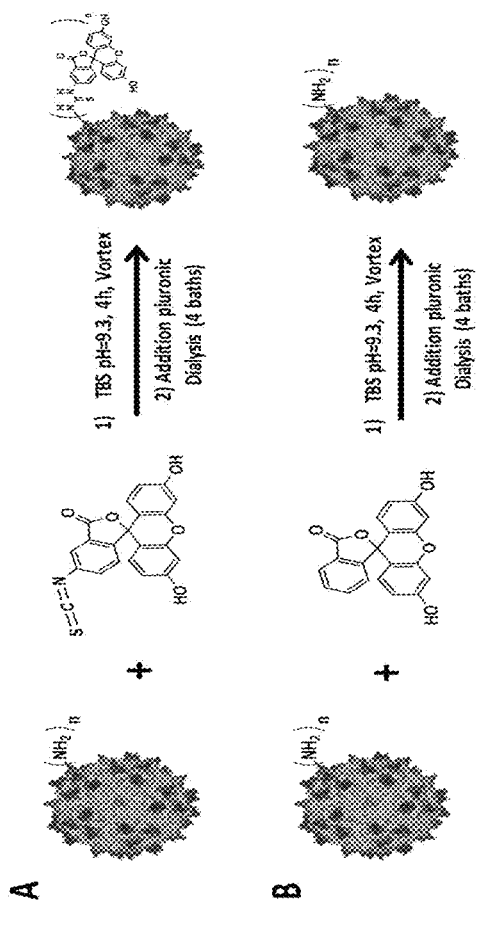
FIG. 1 illustrates the covalent coupling of FITC on the capsid of AAV2 via primary amino groups.
Figure 1:
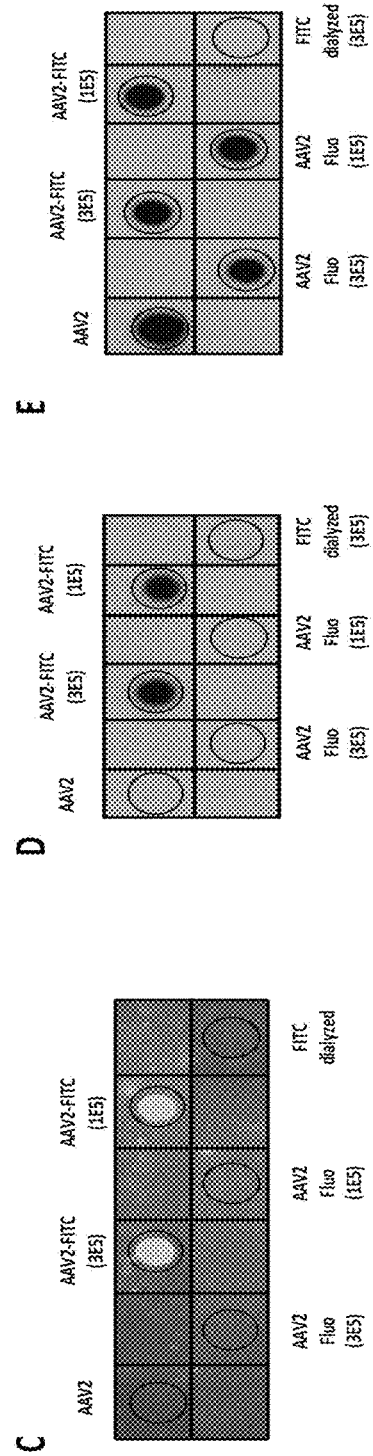

The present invention will now be described with reference to the accompanying drawings, in which representative embodiments of the invention are shown.

Definitions

Unless otherwise indicated, all terms used herein have the same meaning as they would to one skilled in the art, and the practice of the present invention will employ conventional techniques of molecular biology, virology and recombinant DNA technology, which are within the knowledge of those of skill in the art.

The terms "administering," "introducing," or "delivering," as used herein refer to delivery of a plasmid or vector of the invention for recombinant protein or nucleotide expression to a cell or to cells and/or tissues and/or organs of a subject. Such administering, introducing, or delivering may take place in vivo, in vitro, or ex vivo. A plasmid for recombinant protein or polypeptide expression may be introduced into a cell by transfection, which typically means insertion of heterologous DNA into a cell by chemical means (e.g., calcium phosphate transfection, polyethyleneimine (PEI), or lipofection); physical means (electroporation or microinjection); infection, which typically refers to introduction by way of an infectious agent with capacity for replication and/or completing its life cycle, i.e., a virus (e.g., baculovirus expressing AAV Rep genes); or transduction, which in virology refers to infection of a cell without completing the life cycle usually because the required functions for replication of such agent have been modified or the transfer of genetic material from one microorganism to another by way of a viral agent (e.g., a bacteriophage or replication deficient viral vectors).

A vector according to the invention for recombinant polypeptide, protein, or oligonucleotide expression may be delivered by physical means (e.g., calcium phosphate transfection, electroporation, microinjection or lipofection), or by preparing the vector with a pharmaceutically acceptable carrier for in vitro, ex vivo, or in vivo delivery to a cell, tissue, organ, or a subject. Furthermore, a recombinant Adeno-Associated Virus (rAAV) vector particle of the invention can enter cells without the aid of physical means or a carrier (other than the coupled ligand).

The term "host cell" as used herein refers to, for example microorganisms, yeast cells, insect cells, and mammalian cells, that can be, or have been, used as recipients of rAAV vectors. The term includes the progeny of the original cell which has been transduced. Thus, a "host cell" as used herein generally refers to a cell which has been transduced with an exogenous nucleic acid. It is understood that the progeny of a single parental cell may not necessarily be completely identical in morphology or in genomic or total DNA to the original parent, due to natural, accidental, or deliberate mutation.

The term "recombinant" as used herein refers to nucleic acids, vectors, polypeptides, or proteins that have been generated using DNA recombination (cloning) methods and are distinguishable from native or wild-type nucleic acids, vectors, polypeptides, or proteins.

The term "subject" as used herein includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

As used herein the term "tropism" refers to preferential infection and/or transduction of the recombinant Adeno-Associated Virus (rAAV) vector particle of certain cells or tissues. In a preferred embodiment, to modify the AAV particles tropism, the particles are being given certain features such as certain affinities to receptors on the target cell's surface which they do not posses by nature.

The term "pharmaceutically acceptable" as used herein refers to molecular entities and compositions that are physiologically tolerable and do not typically produce toxicity or an allergic or similar untoward reaction, such as gastric upset, dizziness and the like, when administered to a human. Preferably, as used herein, the term "pharmaceutically acceptable" means approved by a regulatory agency of the Federal or a state government or listed in the U. S. Pharmacopeia or other generally recognized pharmacopeia for use in animals, and more particularly in humans.

As used herein the "therapeutic index" is a parameter expressing the therapeutic efficiency of the active drug. It is for example low when implying that high concentration of the active substance is needed to achieve therapeutic efficacy or when the dose required obtaining efficacy induce toxicity. On the contrary, high therapeutic index implies that the dose required of the active substance to provide therapeutic efficacy is low and/or when toxicity of the active drug is low.

The term "chemical modification" as used herein refers to the modification of capsid proteins by chemical reactions and under formation of covalent chemical bonds.

AAV

All recombinant Adeno-Associated Virus may be implemented in the framework of the present invention.

The recombinant Adeno-Associated Virus capsid may be chosen among all identified natural serotypes and in particular AAV2, AAV3b, AAV5, AAV8, AAV9 and AAV10 and may be even more particularly AAV2.

Also, the recombinant Adeno-Associated Virus may be chosen among synthetic serotypes generated by non-natural methods, such as, but not limited to: capsid mutagenesis, peptide insertions into the capsid sequence, capsid shuffling from various serotypes or ancestral reconstruction.

Recombinant AAV are capable of transducing a wide range of post-mitotic cells in vivo in the mammal as muscle cells, hepatocytes or neurons.

Recombinant AAV vectors can be produced by several methods including: transient transfection of HEK293 cells, stable cell lines infected with Ad or HSV, mammalian cells infected with Ad or HSV (expressing rep-cap and transgene) or insect cells infected with baculovirus vectors (expressing rep-cap and transgene). Recombinant AAV vectors produced by any of these methods can be used for the chemical modifications described herein. The vectors may in particular be produced by transient transfection of HEK293 cells with calcium phosphate-HeBS method with two plasmids: pHelper, PDP2-KANA encoding AAV Rep2-Cap2 and adenovirus helper genes (E2A, VA RNA, and E4) and pVector ss-CAG-eGFP as illustrated in example 2.1.

The Recombinant Adeno-Associated Virus of the invention may contain any sequence from extraviral origin as desired.

Capsid

The capsid may naturally or not naturally comprise amino groups. Amino group present at the surface of the capsid is involved in said chemical coupling.

According to a particular embodiment, the Recombinant Adeno Associated Virus vector is composed of wild-type capsid proteins from naturally occurring serotypes.

Said naturally occurring amino groups may be for example lysine, arginine and cysteine, and more particularly lysine.

According to another particular embodiment, the Recombinant Adeno-Associated Virus (rAAV) vector particle is an Adeno Associated Virus with a genetic modification (mutation, insertions or deletions) of the capsid proteins from naturally occurring serotypes or composed by a synthetic capsid.

In the framework of the present invention a synthetic capsid means any combination of capsid proteins from natural or artificially created (random mutations, sequence shuffling, in silico design, etc;) serotypes that are able to assembly and create a new AAV virus capsid that is not existing in nature.

Formula (I)/Ligand L

The invention provides a novel method for chemically modifying an AAV capsid by covalently grafting a ligand L on primary amino groups present on the surface thereof.

The recombinant Adeno-Associated Virus (rAAV) vector particle according to the present invention describes the embodiment where

represents an aromatic moiety forming part of a ligand L, or the embodiment where

is an arylene or an optionally substituted heteroarylene radical, directly or not, covalently bound to at least one ligand L In other words, in this case

is encompassed within the ligand L. As apparent from the examples, proof of concept of the invention was firstly performed through this embodiment.

Still according to this case, the ligand L may be a labeling agent as illustrated in example 2, illustrated by the following formula (A)

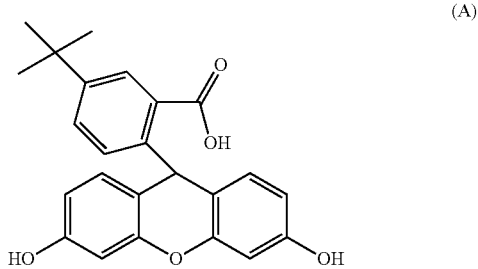 [SMILES: CC(C)(C)c1ccc(C2c3ccc(O)cc3Oc3cc(O)ccc32)c(C(=O)O)c1]

(A)

It is derived from fluorescein and is more particularly derived from fluorescein isothiocyanate (FITC) as reagent of formula (II) as defined herein after.

To this respect, any fluorescent dye comprising an aromatic moiety may also be suitably implemented, such as Rhodamine, Alexa fluor and bodipy.

According to the invention,

does not form part of the ligand L, said ligand L being bound to

, which as a consequence is a divalent group.

According to a particular embodiment,

of formula (I) represents an optionally substituted arylene or heteroarylene radical, directly or not, covalently bound to at least one ligand L.

Typically, the arylene group may be chosen among aromatic cycles like phenylene, naphthylene and anthracenylene, and more particularly among phenylene and naphtylene.

The arylene or heteroarylene group may optionally be substituted by any suitable radical. The following radicals may be cited a halogen atom, a hydroxyl group, an amino group, a ($C_1$-$C_3$) alkyl group or a ($C_1$-$C_3$)alkoxy group.

The arylene group means aromatic cycles comprising from 1 to 3 aromatic rings, for example bicycles or tricycles, in particular fused aromatic rings, from 5 to 20 carbon atoms, in particular from 5 to 12 carbon atoms.

The heteroarylene group means an aromatic cycles comprising from 1 to 3 aromatic rings, in particular fused aromatic rings, from 5 to 20 carbon atoms, in particular from 6 to 10 carbon atoms, optionally comprising at least one heteroatom, for example between 1 and 4 heteroatoms, selected from O, N and S. Examples of monocyclic heteroarylene groups that may be mentioned include imidazolylene, pyrimidylene, isoxazolylene, thiazolylene, isothiazolyl, pyridylene, pyrazolylene, oxazolylene 1,2,4-oxadiazolylene, thienylene and furylene groups.

Pyridylene may more particularly be cited.

Examples of bicyclic heteroarylene groups that may be mentioned include 1H-indazolylene, benzo[1,2,3]thiadiazolylene, benzo[1,2,5]thiadiazolylene, benzothiophenylene, imidazo[1,2-a]pyridylene, quinolinylene, indolylene and isoquinolinylene groups.

In the context of the present invention, and unless otherwise mentioned in the text:
- a halogen atom: a fluorine atom, a chlorine atom, a bromine atom or an iodine atom; in particular, the halogen atom is a fluorine atom;
- an alkyl group: unless otherwise mentioned in the text, a linear or branched saturated aliphatic group containing from 1 to 5 carbons. Examples that may be mentioned include methyl, ethyl, propyl, isopropyl, butyl, isobutyl, tert-butyl and pentyl groups; and
- an alkoxy group: a radical —O-alkyl in which the alkyl group is as defined previously, in particular the alkyl group is a methyl or ethyl.

According to a particular embodiment,

represents a phenlylene group, a napthylene or a pyridylene group and more particularly a group

, a group

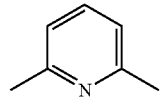

or a group

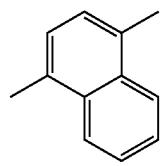

directly or not, covalently bound to at least one ligand L.

The ligand L may fulfill different functions.

Ligand L may typically be chosen among a targeting agent, a steric shielding agent for avoiding neutralizing antibodies interactions, a labeling agent or a magnetic agent.

According to a particular embodiment, ligand L is a targeting ligand, in particular a cell-type specific ligand, and more particularly derived from proteins, from mono- or polysaccharides, from steroid hormones, from RGD motif peptide, from vitamins, from small molecules or from targeting peptide.

According to one embodiment, a cell-type specific ligand may be derived from proteins such as transferring, Epidermal Growth Factor EGF, basic Fibroblast Growth Factor bFGF.

According to one embodiment, a cell-type specific ligand may be derived from mono- or polysaccharides such as galactose, N-acetylgalactosamine and mannose.

According to one embodiment, a cell-type specific ligand may be derived from vitamins such as folates.

According to one embodiment, a cell-type specific ligand may be derived from small molecules including naproxen, ibuprofen or other known protein-binding molecules.

According to one embodiment, a cell-type specific ligand may be derived from a muscle targeting peptide (MTP) comprises an amino acid sequence selected from the group consisting of: ASSLNIA (SEQ ID NO: 1); WDANGKT (SEQ ID NO: 2); GETRAPL (SEQ ID NO: 3); CGHHPVYAC (SEQ ID NO: 4); and HAIYPRH (SEQ ID NO: 5). In certain embodiments, the muscle targeting moiety comprises creatine, from a cancer targeting peptide (CTP) comprises an amino acid sequence derived from linear or cyclic RGD peptides.

According to a more specific aspect of the present embodiment, galactose-derived ligands, which are recognized by asialoglycoprotein receptor (ASPGPr), can be used to specifically target hepatocytes.

In the framework of said specific aspect of the invention and among the moiety of formula (I), mention may be made of a subgroup of moiety of formula (Ia), which may be represented as follows:

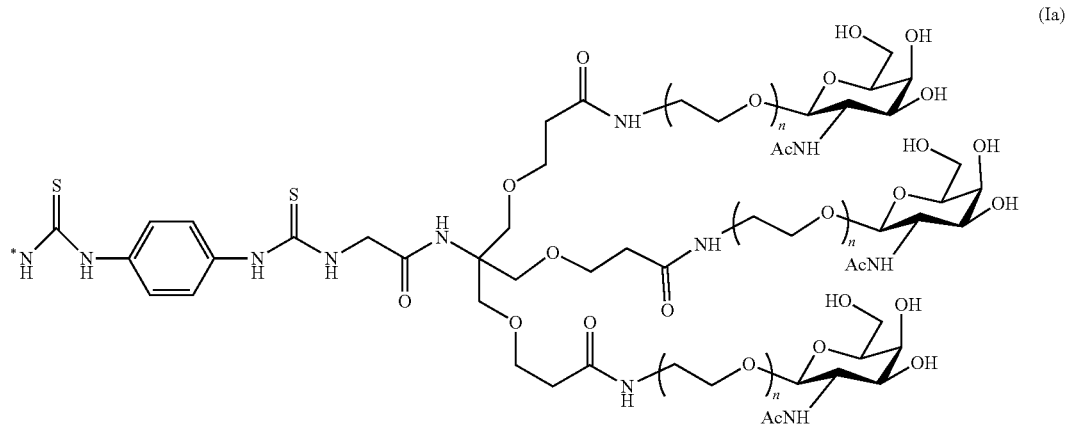

(Ia)

wherein
n ranges from 0 to 5000, in particular from 1 to 2000, and even more particularly from 3 to 100.

Moiety of formula (I) may be selected from

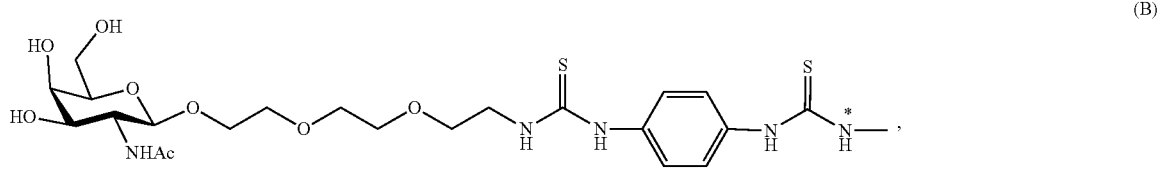

(B)

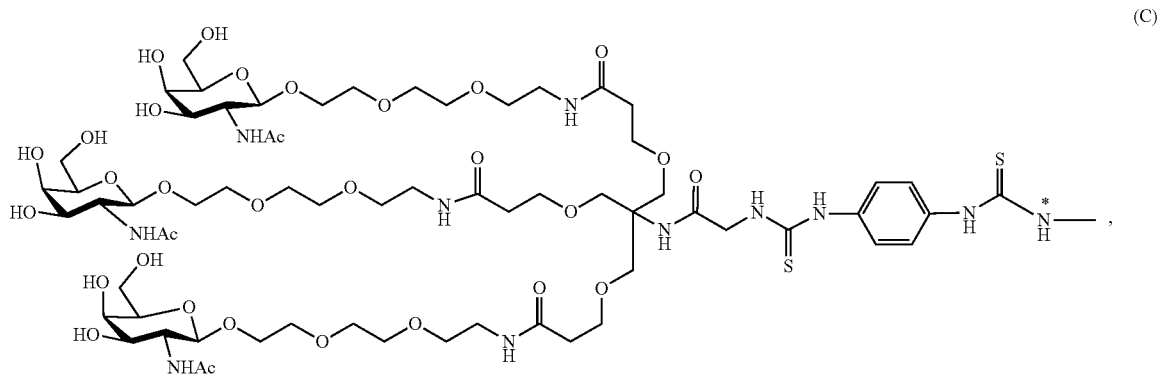

(C)

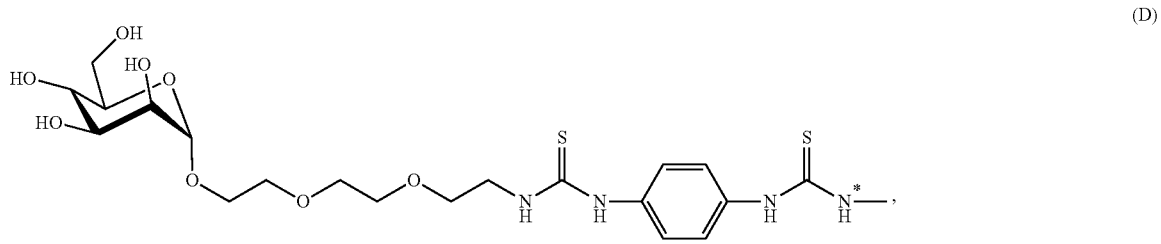

(D)

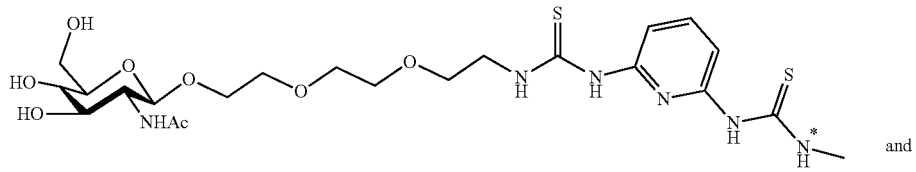

(E)

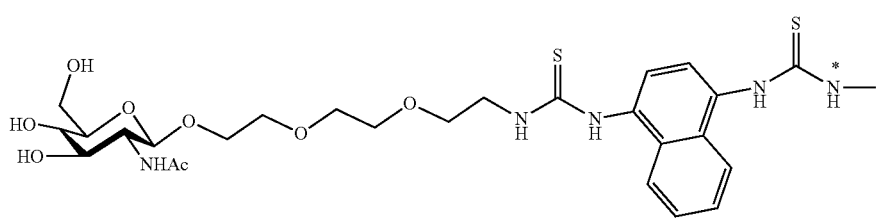

(F)

Said moiety of formula (C) corresponds to a moiety of formula (Ia) wherein n is equal to 3.

According to another particular embodiment, ligand L is a steric shielding agent for avoiding neutralizing antibodies interactions in particular derived from synthetic polymers such as polyethylene glycol (PEG) or pHPMA.

According to a further embodiment, ligand L is a labeling agent, in particular for analytic gene transfer with for example fluorescent dye or nano gold particles, such as Fluorescein, rhodamine, alexa fluor, bodipy or radioactive dye such as $^{18}F$, $^{124,125,131}I$, $^{64}Cu$ or $^{67}Cu$.

According to a further embodiment, the ligand L is a magnetic agent, such as iron particles.

Ligand of various nature may be coupled to the Recombinant Adeno-Associated Virus (rAAV) vector particle by simultaneous or chronological chemical coupling on the capsid.

Method of Coupling

The "coupling" as used herein, refers to the primary amino chemical modification of said primary amino groups as present on the surface of the AAV particle under formation of covalent chemical bonds. Coupling refers to a procedure which maintains the structural integrity of the AAV particle and their core protein functions. Only some primary amino groups on the surface of the capsid are modified.

The coupling may be performed in a buffered aqueous solution.

The incubation time may range between 1 and 24, and more particularly during 4h.

The incubation temperature may range between 20 and 50° C., and even more particularly at room temperature.

The reaction may be carried out in buffer systems with a pH comprised between 7 and 9.6, in particular between 9.2 and 9.4, for example with vortex agitation.

The buffer systems may be selected from TRIS Buffered Saline, sodium carbonate—sodium bicarbonate buffer, PBS, dPBS. The preferred buffer system is TRIS Buffered Saline (TBS).

The amount of reagent of formula (II) may range between 1E5 and 1.5E7 molar equivalent, in particular between 3E5 and 3E6 molar equivalent.

After the step of coupling Pluronic (0.001%) is added on the solution before dialysis.

As a further step, the free molecules may be removed by tangential flow filtration or dialysis (4 baths against dPBS+ 0.001% Pluronic over a period of 24h).

The process may be followed by titration of the particles by qPRC and characterizations (DLS, Dot and Western blot).

The experimental conditions, and more particularly the molar ratio, used for the coupling can modulate the coupling of a ligand on the surface of the capsid of AAV2. It will be used to determine the best ratio which can increase the therapeutic index of these particles.

According to a particular embodiment, the present invention relates to the method for chemically coupling an Adeno-Associated Virus (AAV) vector particle with at least one ligand L, wherein the moiety (L)mX— of B is of formula (III)

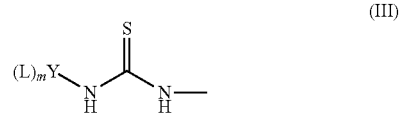

(III)

wherein L is as defined above and Y is a bi- or multivalent organic group, said organic group comprising from 1 to 39 carbon atoms, from 0 to 20 oxygen atoms, from 0 to 6 nitrogen atoms and from 0 to 1 sulfur atoms.

According to a further embodiment, the present invention is dedicated to a method, wherein X represents:

a group

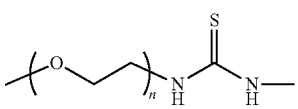

wherein n represents a integer from 0 to 5000, in particular from 1 to 500, from 2 to 100, and even more particularly from 3 to 20, and for example is equal to 3, or a group

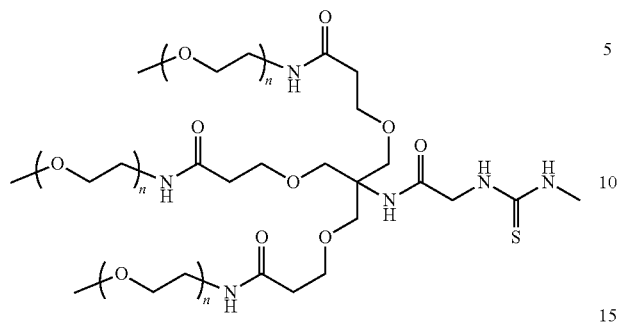

wherein n represents an integer from 0 to 5000, in particular from 1 to 2000, and even more particularly from 3 to 100, and is particularly 3.

The reagents of formula (II) may be obtained according to methods known from the man skilled in the art.

As a way of illustration of the preparation of the reagent of formula (II), useful for obtaining the moiety of formula (B) as described above is detailed hereinafter in scheme 1.

Compound 6 pertaining to formula (II) is obtained, the preparation of which is much more described in example 1 herein after.

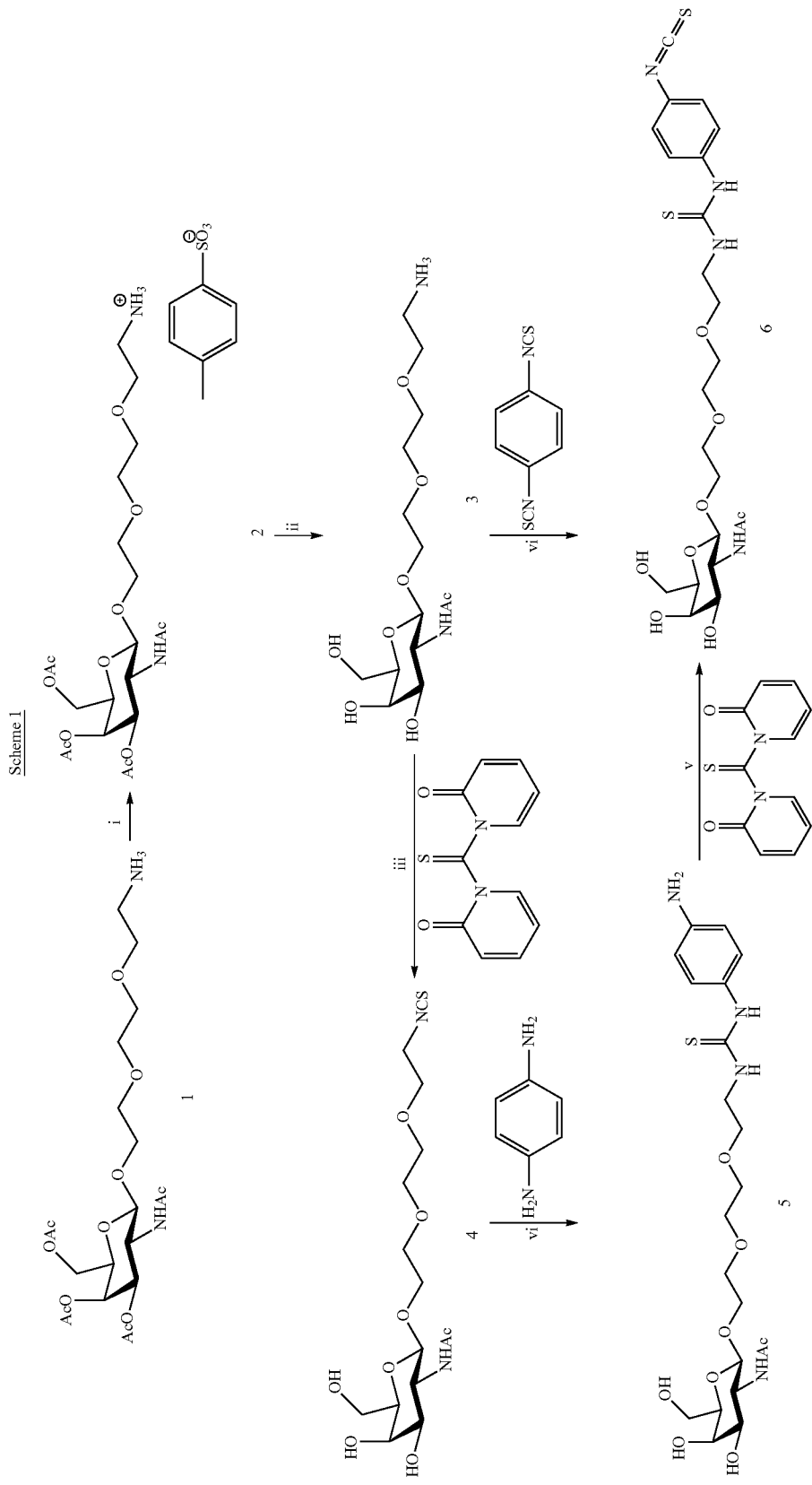
Scheme 1

Compound 1 may be reacted in step (i) with paratoluenesulfonic acid (APTS), in polar solvent for example in ethanol, and more particularly in ethanol under hydrogen atmosphere and in presence of a catalyst, for example Pd—C or Pd(OH)$_2$. The obtained compound 2 may then be reacted in a step (ii) with a strongly basic anion exchange resin, for example Amberlite IRN78, to obtain compound 3.

Method A for the Synthesis of Compound 6

According to a first embodiment, compound 3 may be reacted to afford compound 4 in a step (iii), by reacting 1,1'-thiocarbonyldi-2(1H)-pyridone in a solvent, for example DMF. The obtained compound 4 may then be reacted in a step (iv) with p-phenylendiamine, in a solvent, for example DMF, for example at a temperature ranging from 40 to 100° C., and for example at 60° C., and preferably under inert atmosphere, in particular under nitrogen atmosphere to afford compound 5.

Said compound 5 may then be reacted with 1,1'-thiocarbonyldi-2(1H)-pyridone in a step (v), in a solvent, for example DMF, for example at a temperature ranging from 40 to 100° C., and for example at 60° C., and preferably under inert atmosphere, in particular under nitrogen atmosphere to afford compound 6.

Method B for the Synthesis of Compound 6

According to a second embodiment, compound 3 may be reacted with p-phenylene diisothiocyanate in a step (vi), in a solvent, for example DMF, for example at ambient temperature and preferably under inert atmosphere, in particular under nitrogen atmosphere to afford compound 6.

As a way of illustration of the preparation of the reagent of formula (II), useful for obtaining the moiety of formula (C) as described above is detailed hereinafter in scheme 2. Compound 13 pertaining to formula (II) is obtained, the preparation of which is much more described in example 1 herein after.

Scheme 2
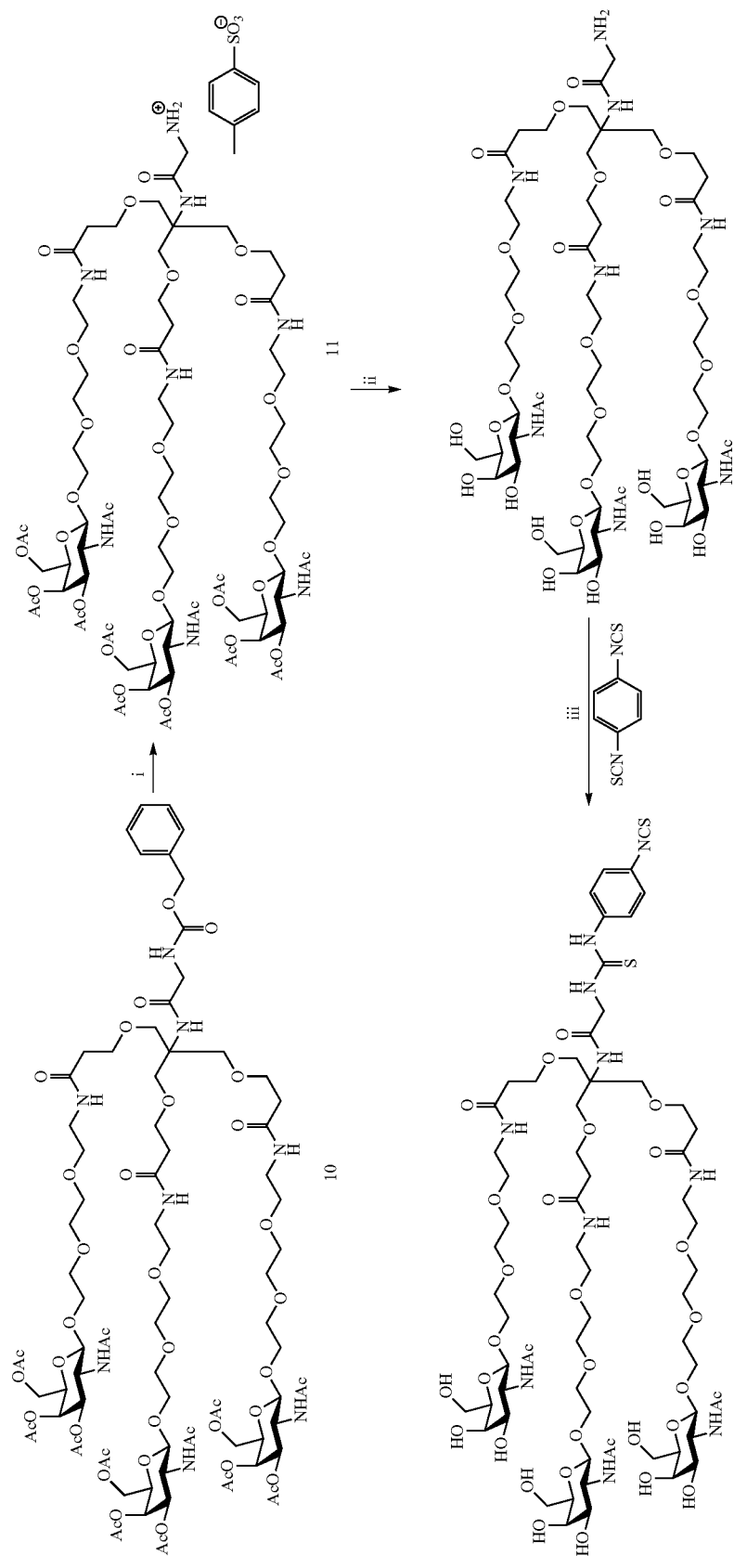

As apparent from scheme 2 above, compound 11 may be dissolved in a solvent, in particular dry ethanol, the it may be reacted with paratoluenesulfonic acid (APTS), in polar solvent and more particularly in ethanol under hydrogen atmosphere and in presence of a catalyst, for example Pd—C or Pd(OH)2. The reaction can then be stirred under hydrogen atmosphere. After a potential filtration and evaporation stage, the reduction of the azoture may be confirmed by TLC and $^1$H NMR spectrometry. The crude product may then be reacted with a strongly basic anion exchange resin, for example Amberlite IRN78, to obtain compound 12.

Compound 12 may be reacted with p-phenylene diisothiocyanate in a step (iii), in a solvent, for example DMF, for example at ambient temperature and preferably under inert atmosphere, in particular under nitrogen atmosphere to afford compound 13.

As a way of illustration of the preparation of the reagent of formula (II), useful for obtaining the moiety of formula (D) as described above is detailed hereinafter in scheme 3. Compound 17 pertaining to formula (II) is obtained, the preparation of which is much more described in example 1 herein after.

Scheme 3

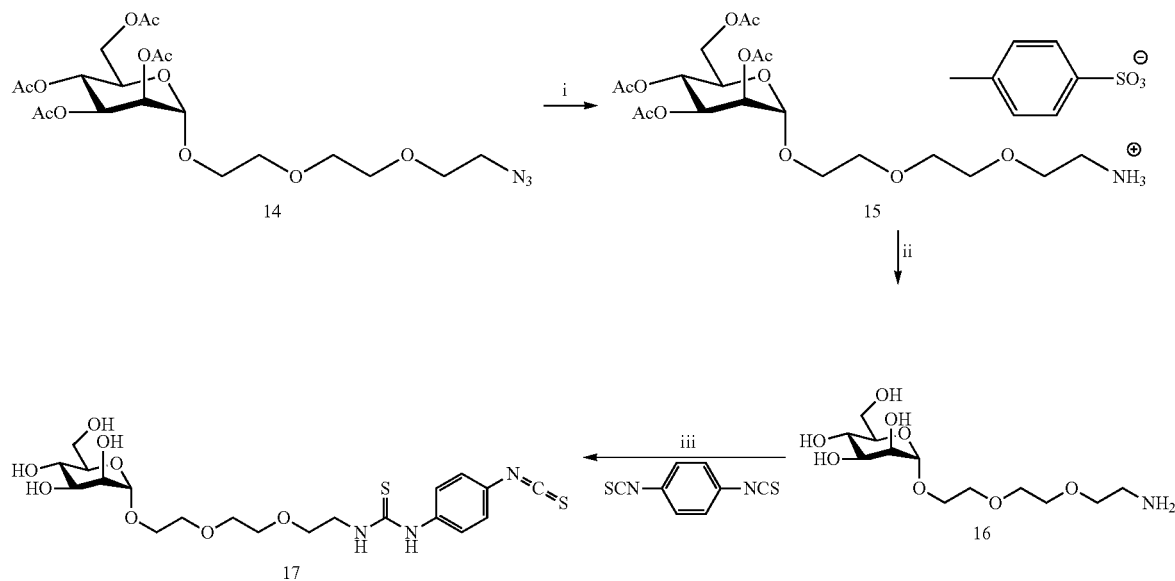

Compound 14 may be reacted in step (i) with paratoluenesulfonic acid (APTS), in polar solvent for example in ethanol, and more particularly in ethanol under hydrogen atmosphere and in presence of a catalyst, for example Pd—C or Pd(OH)$_2$. The obtained compound 15 may then be reacted in a step (ii) with a strongly basic anion exchange resin, for example Amberlite IRN78, to obtain compound 16.

Compound 16 may be reacted with p-phenylene diisothiocyanate in a step (iii), in a solvent, for example DMF, for example at room temperature and preferably under inert atmosphere, in particular under nitrogen atmosphere to generate compound 17.

As a way of illustration of the preparation of the reagent of formula (II), useful for obtaining the moiety of formula (E) and (F) as described above is detailed hereinafter in scheme 4. Compounds 18 and 19 pertaining to formula (II) are obtained, the preparation of which is much more described in example 1 herein after.

Scheme 4

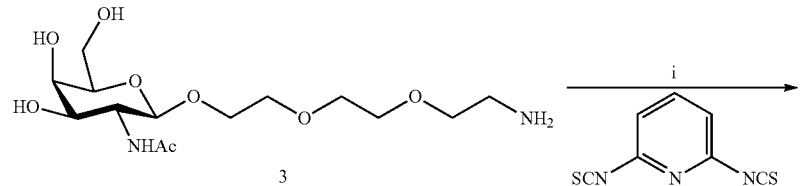

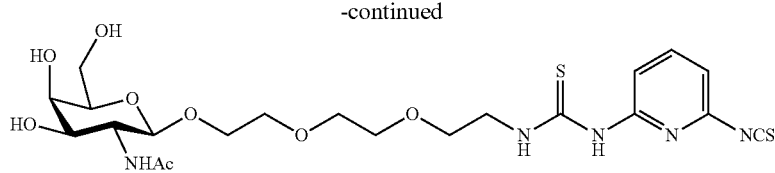

18

Compound 3 may be reacted with 2-6 Pyridine diisothiocyanate in a step (i), in a solvent, for example DMF, for example at room temperature and preferably under inert

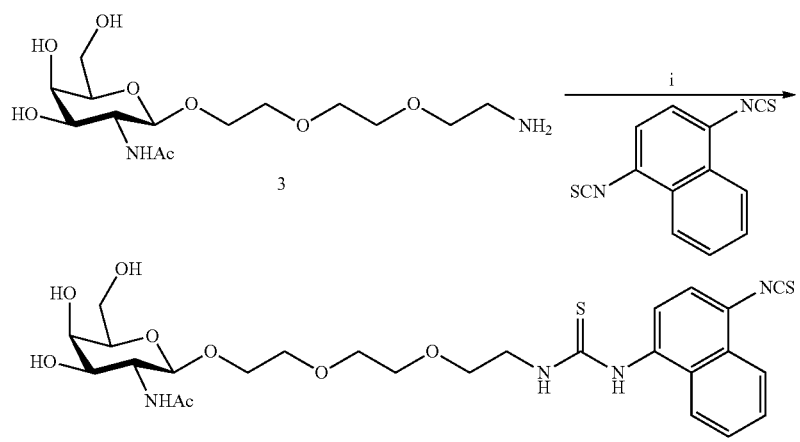

19 atmosphere, in particular under nitrogen atmosphere to generate compound 18.

Compound 3 may be reacted with 1-4 Naphtalene diisothiocyanate in a step (i), in a solvent, for example DMF, for example at room temperature and preferably under inert atmosphere, in particular under nitrogen atmosphere to generate compound 19.

As illustrated in example 2 herein after, the presence of an aromatic moiety between the thiourea function and the ligand L, or within the ligand L when Ar forms part of a ligand L seems to play an important role for the achievement of the grafting of the reagent of formula (II) onto the AAV capsid.

As it also comes out from the example 2, and more particularly example 2.8 the performance of the coupling reaction at a pH greater than 9 seems also to be an essential feature. It may be noticed that the resistance to pH might be dependent on the AAV serotype that has been used. In example 2, the pH>9 was used for AAV2 but other serotypes might have a different susceptibility to pH.

Advantageously, the inventors have found that the obtained rAAV retain infectivity, as illustrated in the examples, and more particularly in example 2.8.

According to a particular embodiment, the obtained Recombinant Adeno-Associated Virus (rAAV) vector particle may be further reacted for modifying the capsid proteins in a second coupling step, in particular by chemical coupling with unreacted amino groups from the first coupling step.

Recombinant Adeno-Associated Virus (rAAV) Vector Particle and its Applications

A Recombinant Adeno-Associated Virus (rAAV) vector particle obtained by a method for producing them according to the present invention also forms part of the present invention.

The cells which the rAAV vectors of the invention target can be derived from a human, and other mammals such as primates, horse, sheep, goat, pig, dog, rat, and mouse.

rAAV vectors can target any cell type, tissue, or organ without limitation. Examples of cells to which rAAV can be delivered into include, but are not limited to, hepatocytes; cells of the retina; i.e. photoreceptors, retinal pigmented epithelium (RPE), bipolar; muscle cells, i.e. myoblasts, satellite cells; cells of the central nervous system (CNS), i.e. neurons, glial; cells of the heart; cells of the peripheral nervous system (PNS); osteoblasts; tumor cells, lymphocytes, and the like. Examples of tissues and organs to which rAAV vectors can be delivered to include liver, muscle, cardiac muscle, smooth muscle, brain, bone, connective tissue, heart, kidney, lung, lymph node, mammary gland, myelin, prostate, testes, thymus, thyroid, trachea, and the like. Preferred cell types are hepatocytes, muscle cells, cells of the CNS, and cells of the PNS. Preferred tissue and organs are liver, muscle, heart, eye, and brain.

The Recombinant Adeno-Associated Virus (rAAV) vector particle according to the present invention may be used for altering the tropism of the Adeno Associated Virus (AAV) vector particle and in particular for targeting to a desired specific organ, tissue or cell types; for accentuating the transduction of a specific cell or tissue or for decreasing the interaction with neutralizing antibodies. This hypothesis is in agreement with data published by Moskalenko et al. (Moskalenko, M., et al., *Epitope mapping of human anti-adeno-associated virus type 2 neutralizing antibodies: implications for gene therapy and virus structure.* J Virol, 2000. 74(4): p. 1761-6) where they have identified a subset of six peptides, which potentially reconstitute a single neutralizing epitope. What is important to note is that three of these peptides are carried by at least one primary amine. The chemical modification of these primary amines could in theory impact favourably on pre-existing sero-neutralization patterns, as already demonstrated for PEGyllated AAV2. (Lee, G. K., et al., *PEG conjugation moderately protects adeno-associated viral vectors against antibody neutralization.* Biotechnol Bioeng, 2005. 92(1): p. 24-34; Le, H. T., et al., *Utility of PEGylated recombinant adeno-associated viruses for gene transfer.* J Control Release, 2005. 108(1): p. 161-77).

According to one embodiment, the Recombinant Adeno-Associated Virus (rAAV) vector particle provides a high cell-type selectivity or high targeting specificity.

Specific organ or tissue may for example be liver, heart, brain, retina or skeletal muscle.

Specific cell type may be for example hepatocytes, cardiomyocytes, myocytes, neurons, retinal pigmented epithelial cells or photoreceptors.

The chemically-modified Recombinant Adeno-Associated Virus (rAAV) vector particle present the advantage of allowing decreasing the therapeutic dose of said Recombinant Adeno-Associated Virus (rAAV) vector particle or improve the efficacy and/or toxicity at the same dose of a non-modified AAV. Said Recombinant Adeno-Associated Virus (rAAV) vector particle according to the present invention may also be advantageous for impairing the humoral response to said Recombinant Adeno-Associated Virus (rAAV) vector particle.

The present invention further relates to the Recombinant Adeno-Associated Virus (rAAV) vector particle according to the invention, for use as a medicament, in particular for delivering therapeutic nucleic acids or for inducing genome editing; as a prophylactic means; as a diagnostic means, such as an imaging agent or for use for efficiency studies for gene therapy.

The Recombinant rAAV vector particle may be used for delivering nucleic acids to target cells.

The Recombinant rAAV vector particle may be administered in vivo or ex vivo.

The Recombinant Adeno-Associated Virus (rAAV) vector particle according to the invention may be dedicated for altering the tropism of the Adeno Associated Virus (AAV) and in particular for targeting to a desired specific organ, tissue or cell types or for accentuating the transduction of a specific cell or tissue.

The Recombinant Adeno-Associated Virus (rAAV) vector particle according to the invention may also be dedicated for impairing the humoral response to said Recombinant Adeno-Associated Virus (rAAV) vector particle.

The Recombinant Adeno-Associated Virus (rAAV) vector particle according to the invention may also be dedicated for decreasing the interaction with neutralizing antibodies.

According to one embodiment, the Recombinant Adeno-Associated Virus (rAAV) vector particle reduces or prevents binding of antibodies to its surface, thereby reducing or preventing its antibody-mediated clearance.

The Recombinant Adeno-Associated Virus (rAAV) vector particle according to the invention may have a selective tropism for hepatocytes, retina, lung, heart, kidney, liver, brain, spleen, tumor or muscle cells, and more particularly for hepatocytes, Retinal Pigmented Epithelium (RPE), photoreceptors, myocytes or cardiomyocytes.

As an illustration of the advantages of the present invention, and as it comes out from the following examples, chemical modification of AAV2 particles allows to overcome some if not all the above limitations classically known when using AAV particles.

Said limitations may be outlined below:

Hepatocyte transduction by AAV2 is low in all mammals, including humans.

To achieve therapeutic benefit it is necessary to inject high doses of vector (~$10^{12}$ AAV2 particles per kg) which may cause an immune toxicity detrimental to the therapeutic effect.

Not only hepatocytes but also other cell types of the liver reticuloendothelial compartment—which accounts for up to 30% of the liver—are transduced by AAV2. This "dispersion" of the transduction profile reduces the therapeutic index of AAV.

Systemic injection of AAV2 induces or activates a T cell response that eventually leads to the elimination of the transduced cells.

More than 80% of human population has neutralizing antibodies against AAV2 precluding efficient transduction unless huge amounts of viral particles are administered.

The introduction of a ligand, a N-acetylgalactosamine (GalNAc) derivative, such as compound 6 and 13 as described above, on the AAV2 particle surface increases the selective transduction of hepatocytes via the asialoglycoprotein receptor (ASPGr).

Among other selective target tissue the following may be cited: the retinal pigmented epithelium (RPE), the skeletal muscle.

The hepatocyte targeting strategy enables to reduce the off-target transduction events in the hepatic reticuloendothelial system as well as other peripheral targets (spleen, heart, lung . . . ). Altogether, the chemical modification according to the present invention results in the improvement of the therapeutic index and also decreases the sensitivity of said Recombinant Adeno-Associated Virus (rAAV) vector particle to preexisting neutralizing antibodies and/or impair the humoral response to the modified capsid.

Thus, according to yet another of its aspects, the present invention further provides a pharmaceutical composition comprising the Recombinant Adeno-Associated Virus (rAAV) vector particle according to the invention, in a pharmaceutically acceptable carrier.

The delivery of said composition to the host cells or target cells may be performed for a variety of therapeutic and other purposes.

The pharmaceutical compositions may contain more particularly an effective dose of at least one Recombinant Adeno-Associated Virus (rAAV) vector particle according to the invention.

An "effective dose" means an amount sufficient to induce a positive modification in the condition to be regulated or treated, but low enough to avoid serious side effects. An effective amount may vary with the pharmaceutical effect to obtain or with the particular condition being treated, the age and physical condition of the end user, the severity of the condition being treated/prevented, the duration of the treatment, the nature of other treatments, the specific compound or composition employed, the route of administration, and like factors.

One of ordinary skill in the art of therapeutic formulations will be able, without undue experimentation and in reliance upon personal knowledge, to ascertain a therapeutically effective dose of a compound of the invention for a given indication.

A pharmaceutical composition of the invention may be formulated with any known suitable pharmaceutically acceptable excipients according to the dose, the galenic form, the route of administration and the likes.

As used herein, "pharmaceutically acceptable excipients" include any and all solvents, dispersion media, coatings, antibacterial and antifungal agents, isotonic and absorption delaying agents and the like. Except insofar as any conventional excipient is incompatible with the active compounds, its use in a medicament or pharmaceutical composition of the invention is contemplated.

The Recombinant Adeno-Associated Virus (rAAV) vector particle of the invention can also be used in a method for the delivery of a nucleotide sequence of interest to a target cell. The method may in particular be a method for delivering a therapeutic gene of interest to a cell of a subject in need thereof.

The invention allows for the in vivo expression of a polypeptide, protein, or oligonucleotide encoded by a therapeutic exogenous DNA sequence in cells in a subject such that therapeutic levels of the polypeptide, protein, or oligonucleotide are expressed.

These results are seen with both in vivo and in vitro modes of Recombinant Adeno-Associated Virus (rAAV) vector particle delivery.

The invention should not be considered limiting with regard to the method of delivery. For example, delivery can be topical, intra-tissue (e.g., intramuscular, intracardiac, intrahepatic, intrarenal, intracerebral), conjunctival (e.g., extra-orbital, intraorbital, retroorbital, intraretinal, sub-retinal), mucosal (e.g., oral, rectal, nasal, pulmonary), intrathecal, intravesical, intracranial, systemic, intraperitoneal, subcutaneous, cutaneous, intravascular (e.g. intravenous, intraarterial), and intralymphatic. In other aspects, passive tissue transduction via high pressure intravascular infusion, e.g. intravenous or intraarterial infusion.

Furthermore, delivery is not limited to one species of rAAV vector. As such, in another aspect, multiple rAAV vectors comprising different exogenous DNA sequences can be delivered simultaneously or sequentially to the target cell, tissue, organ, or subject. Therefore, this strategy can allow for the expression of multiple genes.

According to a particular embodiment of the present invention, the Recombinant Adeno-Associated Virus (rAAV) vector particle is administered intravenously.

Suitable doses of the rAAV may be readily determined by the man skilled in the art, depending upon the condition being treated, the health, age and weight of the subject to be treated, but also depending on the application and on the tissue.

For example for the retina $10^{11}$ vg/patient may be required and for systemic applications like haemophilia, spinal muscular atrophy (SMA) or Duchenne Muscular Dystrophy (DMD) the required dose may be greater than $10^{14}$ vg/patient.

The invention also relates to said Recombinant Adeno-Associated Virus (rAAV) vector particle, for use in a diagnostic method or for use in gene therapy, in particular for treating genetic disorders or acquired disorders inclusing, heart failure, neurological disorders, muscle disorders such as Duchenne Muscular Dystrophy (DMD), liver diseases, blood disorders, metabolic disorders, ocular pathologies or cancer (including retinopathies). Also, said Recombinant Adeno-Associated Virus (rAAV) vector particle can be used for immunotherapies and vaccination.

According to a particular embodiment, said Recombinant Adeno-Associated Virus (rAAV) vector particle is more particularly useful for the indications selected from hepatic, retinal and neuromuscular genetic diseases.

The present invention additionally relates to a method for delivering rAAV of the invention to a subject in need thereof, comprising at least one step of administration of a composition comprising at least one rAAV of the invention.

The present invention will be better understood by referring to the following examples and figures which are provided for illustrative purpose only and should not be interpreted as limiting in any manner the instant invention.

EXAMPLES

Material

All chemical reagents were purchased from Acros Organics or Aldrich and were used without further purification. AAV capsid proteins (B1), rabbit polyclonal and mouse monoclonal A20 were obtained from PROGEN Biotechnik. Anti-Fluorescein-AP, Fab fragments (Sigma-Aldrich) for the detection of fluorescein-labeled compounds was obtained from Roche. FITC-Soybean Agglutinin (SBA) was purchased from Vector laboratories. Reactions requiring anhydrous conditions were performed under nitrogen. All compounds were fully characterized by $^1$H (400.133 or 300.135 MHz), $^{13}$C (125.773 or 75.480 MHz) NMR spectroscopy (Bruker Avance 300 Ultra Shield or Bruker Avance III 400 spectrometer). Chemical shifts are reported in parts per million (ppm); coupling constant are reported in units of Hertz [Hz]. The following abbreviations were used: s=singlet, d=doublet, t=triplet, q=quartet, quin=quintet, br=broad singlet. When needed, $^{13}$C heteronuclear HMQC and HMBC were used to unambiguously establish structures. High-resolution mass spectra (HRMS) were recorded with a Thermofisher hybrid LTQ-orbitrap spectrometer (ESI$^+$) and a Bruker Autoflex III SmartBeam spectrometer (MALDI).

All the products were purified by flash chromatography (GRACE REVELERIS Flash Chromatography System) equipped with UV and DLS detectors.

Compound 13 has been purified by HPLC using UPLC H-Class from Waters.

Example 1: Synthesis of the Reagent of Formula (II) and Comparative Reactants

Scheme for the Synthesis of Comparative Reactant 9

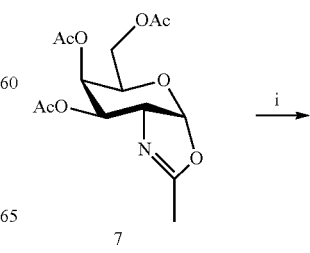

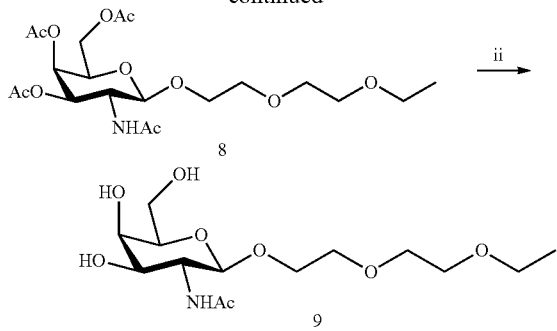

i: DCM, 2-(2-Ethoxyethoxy)ethanol, molecular sieves; ii: MeOH/H₂O, IRN78.

Scheme for the Synthesis of Comparative Reactant 22

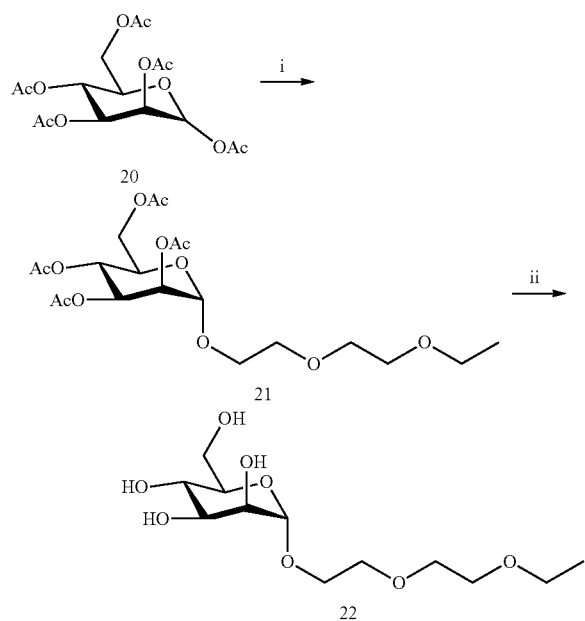

i: DCM, 2-(2-Ethoxyethoxy)ethanol, SnCl₄, TFA-Ag:
ii: MeOH/H₂, IRN78.

Compounds 1, 7, 10, 2,6 pyridine diisothiocyanate and 1,4 naphtalene diisothiocyanate as already defined above in the description, were synthetized according to the literature and more particularly according to the two following article and patent:

[1] Rensen P C et al. "Design and synthesis of novel N-acetylgalactosamine-terminated glycolipids for targeting of lipoproteins to the hepatic asialoglycoprotein receptor". Journal of medicinal chemistry. 2004; 47:5798-808, and
[2] Rajeev K G, et al. "Inhibitory RNA interference agents modified with saccharide ligands" Patent WO 2012037254. 2012.
[3] Chevolot Y, et al. "DNA-Based Carbohydrate Biochips: A Platform for Surface Glyco-Engineering". Angewandte Chemie International Edition, 2007; 46:2398-2402.
[4] Nagarajan, K., et al. "Quest for anthelmintic agents. Part I. Para substituted phenylisothiocyanates, heterocyclyli sothiocyanates and bisisothiocyanates,". Indian Journal of Pharmaceutical Sciences, 48(3), 53-9; 1986.

1 (284 mg, 0.56 mmol) was dissolved in dry ethanol, then APTS (107 mg, 0.56 mmol) was added followed by the addition of 10% of Pd—C(10% w). After three vacuum/H₂ cycles the reaction was stirred overnight at 20° C. under H₂ atmosphere. The solution was then filtrated and evaporated under reduce pressure. The reduction of the azoture was confirmed by TLC and $^1$H NMR. After evaporation, 10 mL of methanol and 10 mL of water were added to the crude product, followed by the addition of Amberlite IRN78 resin. The reaction was stirred 3h at 20° C., then filtrated and evaporated under reduce pressure. (yield: 3=77%).

Compound 3: $^1$H NMR (MeOD): 2.0 (s, 3H, NAc), 2.79 (t, 2H, CH₂NH₂, $J_{H-H}$=5.2 Hz), 3.4-4.0 (m, 16H, CH₂O, H-2, H-3, H-4, H-5, H-6), 4.44 (d, 1H, H-1, $J_{1-2}$=8.4 Hz); $^{13}$C NMR (MeOD): 23.1, 42.1, 54.3, 62.6, 69.7, 69.8, 71.3, 71.5, 71.6, 73.5, 73.6, 76.8, 103.1, 174.2; HRMS (MALDI) for $C_{14}H_{29}N_2O_8$ [M+H]⁺, calcd 353.1924 found 353.1918.

Compound 3 (162 mg, 0.46 mmol) was dissolved in dry DMF, then 1,1'-thiocarbonyldi-2(1H)-pyridone (117 mg, 0.51 mmol) was added and the reaction was stirred overnight at 20° C. under N₂ atmosphere. The solution was then evaporated under reduce pressure and purified by flash chromatography (DCM/MeOH from 100/0 to 80/20). (yield: 4=88%).

Compound 4: $^1$H NMR (MeOD): 2.0 (s, 3H, NAc), 3.4-4.0 (m, 19H, CH₂O, CH₂NCS, H-2, H-3, H-4, H-5, H-6), 4.44 (d, 1H, H-1, $J_{1-2}$=8.4 Hz); $^{13}$C NMR (MeOD): 23.1, 46.3, 54.3, 62.6, 69.7, 69.8, 70.5, 71.5, 71.6, 73.5, 73.6, 76.8, 103.1, 133.2, 174.2; HRMS (MALDI) for $C_{15}H_{26}N_2O_8NaS$ [M+Na]⁺, calcd 417.1308 found 417.1318.

Method a for the Synthesis of 6

4 (50 mg, 0.13 mmol) was dissolved in dry DMF, then p-phenylenediamine (28 mg, 0.26 mmol) was added and the reaction was stirred overnight at 70° C. under N₂ atmosphere. The solution was then evaporated under reduce pressure and purified by flash chromatography (DCM/MeOH from 100/0 to 80/20). (yield: 5=74%).

Compound 5: $^1$H NMR (MeOD): 1.97 (s, 3H, NAc), 3.4-4.0 (m, 17H, CH₂O, H-2, H-3, H-4, H-5, H-6), 4.43 (d, 1H, H-1, $J_{1-2}$=8.4 Hz), 6.72 (d, 2H, =8.8 Hz), 6.98 (d, 2H, $J_{H-H}$=8.8 Hz); $^{13}$C NMR (MeOD): 23.1, 45.4, 54.4, 62.6, 69.7, 69.8, 70.4, 71.4, 71.5, 71.6, 73.4, 76.8, 103.1, 2*116.9, 2*128.1, 128.3, 148.3, 174.1, 182.4; HRMS (MALDI) for $C_{21}H_{35}N_4O_8S$ [M+H]⁺, calcd 503.2176 found 503.2171.

5 (47 mg, 0.093 mmol) was dissolved in dry DMF, then 1,1'-thiocarbonyldi-2(1H)-pyridone (24 mg, 0.102 mmol) was added and the reaction was stirred overnight at 60° C. under N₂ atmosphere. The solution was then evaporated under reduce pressure and purified by flash chromatography (DCM/MeOH from 100/0 to 80/20). (yield: 6=60%).

Compound 6: $^1$H NMR (MeOD): 1.99 (s, 3H, NAc), 3.4-4.0 (m, 17H, CH₂O, H-2, H-3, H-4, H-5, H-6), 4.42 (d, 1H, H-1, $J_{H-H}$=8.4 Hz), 7.24 (d, 2H, =8.8 Hz), 7.54 (d, 2H, $J_{H-H}$=8.8 Hz); $^{13}$C NMR (MeOD): 23.2, 45.4, 54.3, 62.6, 69.7, 69.9, 70.3, 71.4, 71.5, 71.6, 73.4, 76.8, 103.2, 2*125.8, 2*127.1, 128.5, 136.6, 139.8, 174.2, 182.5; HRMS (MALDI) for $C_{22}H_{33}N_4O_8S_2$ [M+H]⁺, calcd 545.1740 found 545.1742.

Method B for the Synthesis of 6

3 (64 mg, 0.18 mmol) was dissolved in dry DMF, then p-phenylene diisothiocyanate (175 mg, 0.9 mmol) was added and the reaction was stirred during 2h at 20° C. under N₂ atmosphere. The solution was then evaporated under reduce pressure and purified by flash chromatography (DCM/MeOH from 100/0 to 80/20). (yield: 6=85%).

Compound 6: ¹H NMR (MeOD): 1.99 (s, 3H, NAc), 3.4-4.0 (m, 17H, CH$_2$O, H-2, H-3, H-4, H-5, H-6,), 4.42 (d, 1H, H-1, J$_{H-H}$=8.4 Hz), 7.24 (d, 2H, J$_{H-H}$=8.8 Hz), 7.54 (d, 2H, J$_{H-H}$=8.8 Hz); ¹³C NMR (MeOD): 23.2, 45.4, 54.3, 62.6, 69.7, 69.9, 70.3, 71.4, 71.5, 71.6, 73.4, 76.8, 103.2, 2*125.8, 2*127.1, 128.5, 136.6, 139.8, 174.2, 182.5; HRMS (MALDI) for C$_{22}$H$_{33}$N$_4$O$_8$S$_2$ [M+H]$^+$, calcd 545.1740 found 545.1742.

Compound 7 (981 mg, 2.98 mmol) was dissolved in dry DCM, then 2-(2-Ethoxyethoxy)ethanol (404 µL, 2.98 mmol) and molecular sieves were added and the solution was stirred during 0.5h at 20° C. under N$_2$ atmosphere. TMSOTf (270 µL, 1.49 mmol) was then added to the solution at 0° C. under N$_2$ atmosphere. The solution was stirred 0.5h at 0° C. and overnight at 20° C. under N$_2$ atmosphere. After evaporation the residue was dissolved in DCM, washed respectively with saturated aqueous NaHCO$_3$, water and brine, dried over MgSO$_4$, filtered and evaporated. The solution was then evaporated under reduce pressure and purified by flash chromatography (DCM/MeOH from 100/0 to 95/5). (yield: 8=73%).

Compound 8: ¹H NMR (MeOD): 1.19 (t, 3H, CH$_3$, J$_{H-H}$=7.2 Hz), 1.93 (s, 3H, OCH$_3$), 1.94 (s, 3H, OCH$_3$), 2.03 (s, 3H, OCH$_3$), 2.14 (s, 3H, NAc), 3.5-4.2 (m, 14H, CH$_2$O, H-2, H-5, H-6), 4.67 (d, 1H, H-1, J$_{1-2}$=8.4 Hz), 5.04 (dd, 1H³, J$_{3-4}$=3.2 Hz, J$_{3-2}$=11.2 Hz), 5.33 (d, 1H-4, J$_{3-4}$=3.2 Hz); ¹³C NMR (MeOD): 15.4, 20.5, 2*20.6, 22.9, 51.6, 54.8, 62.7, 67.6, 68.2, 70.0, 70.9, 71.6, 71.8, 72.3, 102.8, 171.7, 2*172.1, 173.5; HRMS (MALDI) for C$_{20}$H$_{34}$NO$_{11}$ [M+H]$^+$, calcd 464.2132 found 464.2141.

Compound 8 was dissolved in 10 mL of methanol and 10 mL of water, then Amberlit IRN78 resin was added. The mixture was stirred 3h at 20° C., then filtrated and evaporated under reduce pressure. (yield: 9=77%).

Compound 9: ¹H NMR (MeOD): 1.2 (t, 3H, =6.8 Hz), 1.99 (s, 3H, NAc), 3.4-4.0 (m, 16H, CH$_2$O, H-2, H-3, H-4, H-5, H-6), 4.45 (d, 1H, H-1, J$_{1-2}$=8.4 Hz); ¹³C NMR (MeOD): 15.4, 23.1, 54.3, 62.6, 67.6, 69.7, 69.8, 71.0, 71.6, 71.7, 73.6, 76.8, 103.1, 174.2; HRMS (MALDI) for C$_{14}$H$_{28}$NO$_8$ [M+H]$^+$, calcd 338.1815 found 338.1819.

Compound 10 (100 mg, 0.052 mmol) was dissolved in dry ethanol, then APTS (10 mg, 0.052 mmol) was added followed by the addition of Pd—C(10% w). After three vacuum/H$_2$ cycles the reaction was stirred overnight at 20° C. under H$_2$ atmosphere. The solution was then filtrated and evaporated under reduce pressure. The reduction of the azoture was confirmed by TLC and ¹H NMR. After evaporation, 10 mL of methanol and 10 mL of water were added to the crude product, followed by the addition of Amberlite IRN78 resin. The reaction was stirred 3h at 20° C., then filtrated and evaporated under reduce pressure. (yield: 12=76%).

Compound 12: ¹H NMR (MeOD): 1.99 (s, 9H, NAc), 2.79 (t, 6H, CH$_2$CO, J$_{H-H}$=6 Hz), 3.22 (s, 2H, CH$_2$NH$_2$), 3.4-4.0 (m, 66H, CH$_2$O, H-2, H-3, H-4, H-5, H-6), 4.44 (d, 3H, H-1, J$_{1-2}$=8.4 Hz), ¹³C NMR (MeOD): 3*23.1, 3*37.6, 3*40.4, 45.7, 3*54.3, 61.2, 3*62.6, 3*68.0, 3*69.7, 3*69.8, 3*70.2, 3*70.7, 3*71.4, 3*71.5, 3*71.6, 3*73.5, 3*76.8, 3*130.1, 3*174.0, 3*174.1, 175.35; HRMS (MALDI) for C$_{57}$H$_{105}$N$_8$O$_{31}$ [M+H]$^+$, calcd 1397.6886 found 1397.6803.

Compound 12 (64 mg, 0.18 mmol) was dissolved in dry DMF, then p-phenylene diisothiocyanate (175 mg, 0.9 mmol) was added and the reaction was stirred during 2h at 20° C. under N$_2$ atmosphere. The solution was then evaporated under reduce pressure. The crude was first washed with DCM to remove the majority of the p-phenylene diisothiocyanate and then purified by preparative HPLC. (yield: 13=8%).

Compound 13: ¹H NMR (MeOD): 2.00 (s, 9H, NAc), 2.46 (t, 6H, CH$_2$CO, J$_{H-H}$=6 Hz), 3.30-4.20 (m, 66H, CH$_2$O, H-2, H-3, H-4, H-5, H-6), 4.28 (s, 2H, CH$_2$NH$_2$), 4.46 (d, 3H, H-1, J$_{1-2}$=8.4 Hz), 7.29 (d, 2H, J$_{H-H}$=9 Hz), 7.60 (d, 2H, J$_{H-H}$=9 Hz); HRMS (MALDI) for C$_{65}$H$_{108}$N$_{10}$O$_{31}$NaS$_2$ [M+Na]$^+$, calcd 1611.6521 found 1611.6487.

14 (250 mg, 0.49 mmol) was dissolved in dry ethanol, then APTS (94.1 mg, 0.49 mmol) was added followed by the addition of 10% of Pd—C(10% w). After three vacuum/H$_2$ cycles the reaction was stirred overnight at 20° C. under H$_2$ atmosphere. The solution was then filtrated and evaporated under reduce pressure. The reduction of the azoture was confirmed by TLC and ¹H NMR. After evaporation, 10 mL of methanol and 10 mL of water were added to the crude product, followed by the addition of Amberlite IRN78 resin. The reaction was stirred 3h at 20° C., then filtrated and evaporated under reduce pressure. (yield: 16=86%).

Compound 16: ¹H NMR (MeOD): 2.80 (t, 2H, CH$_2$NH$_2$, J$_{H-H}$=5.4 Hz), 3.5-4.0 (m, 16H, CH$_2$O, H-2, H-3, H-4, H-5, H-6), 4.81 (d, 1H, H-1, J$_{1-2}$=1.8 Hz); HRMS (MALDI) for C$_{12}$H$_{26}$NO$_8$ [M+H]$^+$, calcd 311.1603 found 311.1600.

16 (105 mg, 0.34 mmol) was dissolved in dry DMF, then p-phenylene diisothiocyanate (325 mg, 1.7 mmol) was added and the reaction was stirred during 2h at 20° C. under N$_2$ atmosphere. The solution was then evaporated under reduce pressure and purified by flash chromatography (DCM/MeOH from 100/0 to 80/20). (yield: 17=85%).

Compound 17: ¹H NMR (MeOD): 3.5-4.0 (m, 18H, CH$_2$O, CH$_2$N, H-2, H-3, H-4, H-5, H-6), 4.82 (d, 1H, H-1, J$_{1-2}$=1.8 Hz); 7.26 (d, 2H, J$_{H-H}$=8.8 Hz), 7.52 (d, 2H, =8.8 Hz); HRMS (MALDI) for C$_{20}$H$_{29}$N$_3$O$_8$NaS$_2$ [M+Na]$^+$, calcd 526.1302 found 526.1294.

3 (25 mg, 0.071 mmol) was dissolved in dry DMF, then 2,6 pyridine diisothiocyanate (68 mg, 0.9 mmol) was added and the reaction was stirred during 2h at 20° C. under N$_2$ atmosphere. The solution was then evaporated under reduce pressure washed several times with CH$_3$CN and DCM. (yield: 18=42%).

Compound 18: ¹H NMR (DMSO): 1.79 (s, 3H, NAc), 3.2-4.6 (m, 18H, CH$_2$O, H-2, H-3, H-4, H-5, H-6,), 4.28 (d, 1H, H-1, J$_{1-2}$=8.4 Hz), 7.07 (d, 1H, J$_{H-H}$=7.5 Hz), 7.16 (d, 1H, J$_{H-H}$=8.1 Hz), 7.60 (m, NH), 7.86 (t, 1H, J$_{H-H}$=8.1 Hz); HRMS (MALDI) for C$_{21}$H$_{32}$N$_5$O$_8$S$_2$ [M+H]$^+$, calcd 546.1697 found 546.1692.

3 (25 mg, 0.071 mmol) was dissolved in dry DMF, then 1,4 naphtalene diisothiocyanate (86 mg, 0.355 mmol) was added and the reaction was stirred during 2h at 20° C. under N$_2$ atmosphere. The solution was then evaporated under reduce pressure and purified by flash chromatography (DCM/MeOH from 100/0 to 80/20). (yield: 19=58%).

Compound 19: ¹H NMR (DMSO): 1.80 (s, 3H, NAc), 3.2-4.6 (m, 18H, CH$_2$O, H-2, H-3, H-4, H-5, H-6,), 4.29 (d, 1H, H-1, J$_{1-2}$=8.4 Hz), 7.6-8.1 (m, 8H, ⁶H$_{arom}$, 2 NH), 9.83 (m, 1H, NH); HRMS (MALDI) for C$_{26}$H$_{34}$N$_4$O$_8$NaS$_2$ [MNa]$^+$, calcd 617.1717 found 617.1716.

Compound 20 (500 mg, 1.28 mmol) was dissolved in dry DCM, then 2-(2-Ethoxyethoxy)ethanol (174 µL, 1.28 mmol) and TFA-Ag (424 mg, 1.92 mmol) were added in the solution. SnCl$_4$ (1M in CH$_2$Cl$_2$, 3.84 mL, 3.84 mmol) was added dropwise (within 30 min) at room temperature to the stirred solution and was stirred during 3h at 20° C. under N$_2$ atmosphere. The solution was then washed respectively with saturated aqueous NaHCO$_3$, water and brine, dried over MgSO$_4$ and filtered. The solution was then evaporated under reduce pressure and purified by flash chromatography (DCM/MeOH from 100/0 to 95/5). (yield: 21=73%). The glycosylation was confirmed by TLC and mass spectroscopy and then compound 21 (150 mg, 0.323 mmol) was dissolved in 10 mL of methanol and 10 mL of water, then Amberlit IRN78 resin was added. The mixture was stirred 3h at 20° C., then filtrated and evaporated under reduce pressure. (yield: 22=77%).

Compound 22: $^1$H NMR (MeOD): 1.19 (t, 3H, $J_{H-H}$=6.9 Hz), 3.4-4.0 (m, 16H, $CH_2O$, H-2, H-3, H-4, H-5, H-6), 4.79 (d, 1H, H-1, $J_{1-2}$=1.8 Hz); HRMS (MALDI) for $C_{20}H_{29}N3O_8NaS_2$ $[M+Na]^+$, calcd 526.1302 found 526.1294.

Example 2: Transduction of Human Primary Hepatocytes by a Chemically Modified AAV2

2.1. AAV2 Production and Purification

AAV2 vectors were produced from two plasmids: pHelper, PDP2-KANA encoding AAV Rep2-Cap2 and adenovirus helper genes (E2A, VA RNA, and E4) and pVector ss-CAG-eGFP. All vectors were produced by transient transfection of HEK293 cells with calcium phosphate-HeBS method. Vector produced cells were harvested for 48 hours after transfection and treated firstly with Triton-1% and benzonase (25U/mL) for 1 hour at 37° C. After 1 h of incubation at 37° C., the bulk was centrifuged at 2000 rpm for 20 min and subjected to freeze-thaw cycles to release vector particles. The cellular debris was removed by centrifugation at 2500 rpm for 15 min. Cell lysates were precipitated with PEG overnight and clarified by centrifugation at 4000 rpm for 1 hour. The precipitates were then incubated with benzonase for 30 min at 37° C. and collected after centrifugation at 10000 g for 10 min at 4° C. Vectors were purified by double cesium chloride (CsCl) gradient ultracentrifugation. The viral suspension was then subjected to four successive rounds of dialysis under slight stirring in a Slide-a-Lyzer cassette (Pierce) against dPBS (containing $Ca^{++}$ and $Mg^{++}$).

2.2. Coupling and Purification (According to the Invention and with Comparative Reactants)

AAV2-GFP (1E12 vg, 2.49 nmol) was added to a solution of TRIS buffer pH=9.3 containing fluorescein isothiocyanate (FITC) of formula

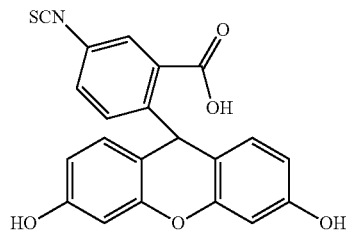

(outside invention), 6 (invention), 9(comparative), 13 (invention), 16 (comparative), 17 (invention), 18 (invention), 19 (invention) or 22 (comparative) at different molar ratios (from 3E5 to 1.5E7 equivalents) and incubated during 4h at 20° C. The solutions containing the vectors were then dialyzed against dPBS+0.001% Pluronic to remove free molecules that were non-binded to the AAV capsid.

2.3. Viral Genome Extraction

3 μL of AAV2 or chemically modified AAV2 were treated with 20 units of DNase I (Roche #04716728001) at 37° C. for 45 min to remove residual DNA in vector samples. After the treatment with DNase I, 20 μL of proteinase K 20 mg/mL (MACHEREY-NAGEL #740506) was then added and incubated at 70° C. for 20 min. Extraction column (NucleoSpin® RNA Virus) were then used to extract DNA from purified AAV vectors.

2.4. Quantitative Real Time PCR Analysis

Quantitative real time PCR (qPCR) was performed with a StepOnePlus™ Real-Time PCR System Upgrade (Life technologies). All PCRs were performed in a 20 μL final volume PCR including primers, probe, PCR Master Mix (TaKaRa) and 5 μL of template DNA (plasmid standard, or sample DNA). qPCR was carried out with an initial denaturation step at 95° C. for 20 seconds, followed by 45 cycles of denaturation at 95° C. for 1 second and annealing/extention at 56° C. for 20 seconds. Plasmid Standard were generated with seven serial dilutions (containing $10^8$ to $10^2$ copies of plasmid) of a plasmid pTR-UF-11 (ATCC® MBA-331™) linearized by Sca-I Restriction Enzyme.

2.5. Western Blotting

All vectors were denatured at 100° C. using laemmli sample buffer for 5 min and separated by SDS-PAGE 10% Tris-Glycine polyacrylamide gels (Life Technologies). Precision plus Protein All Blue Standards (BioRad) was used as a molecular-weight size marker. After transferring the proteins to nitrocellulose membrane using a Transfer buffer (25 mM tris/192 mM Glycine/0.1 (w/v) SDS/20% MeOH) for 1 hour at 150 mA in a Trans-Blot SD Semi-Dry Transfer Cell (Bio-Rad), the membrane was saturated with 5% semi-skimmed milk in PBS-Tween (0.1%) or with 1% gelatin, 0.1% Igepal in PBS-Tween (0.01%) during 2h at RT. After saturation, the membrane was probed with antisera to AAV2 and chemically modified AAV2 (polyclonal, B1 monoclonal or Anti-Fluorescein-AP) or with FITC-Soybean Agglutinin or FITC-Concanavalin A overnight at 4° C. Three washings were carried out between each stage to remove unbound reagents with PBS-Tween (0.1%) for 15 min at RT. Bands were visualized by chemiluminescence using alkaline phosphatase (AP) or horseradish peroxidase (HRP) conjugated secondary antibodies and captured on X-ray film.

2.6. Immuno Dot-Blot

Non-denatured AAV2 and chemically modified AAV2 were deposited on a nitrocellulose paper soaked briefly in PBS prior to assembling the dot blot manifold (Bio-Rad). Nitrocellulose membrane was treated as for western blotting.

2.7. Dynamic Light Scattering

DLS was done using a Malvern zetasizer nano ZS. The calibration was controlled beforehand by using 30 and 300 nm solution of Nanosphere size standard. 50 μL of each vectors were placed in a specific cuvette DTS0118 from Malvern and analysed by volume.

2.8. Transduction of Human and Murine Primary Hepatocytes

Murine and human primary hepatocytes and culture medium were purchased from BTOPREDIC international (Rennes, FRANCE). Murine and human hepatocytes were seeded on a 24-well plastic surface at a density of approximately 2.5E5 cells/well. After reception, cell culture medium was removed and replaced with 1 mL of basal medium (MIL600) with additives (ADD222) and incubated 2h in 37° C.-5% $CO_2$. Murine or human primary hepatocytes were transduced at MOI of 1E5 by AAV3b, AAV2 or chemically modified AAV2 vectors in 0.5 mL of culture medium as indicated in the examples. Six hours after the transduction 0.5 mL of fresh culture medium was added in each well. All AAV vectors encoded for GFP. The culture plates were incubated for 48 hours at 37° C.-5% $CO_2$ before flow cytometry analysis of GFP positives cells. Cells were dissociated with Trypsin-EDTA (Sigma-Aldrich), fixed with 4% paraformaldehyde and analysed by BD-LSRII Flow Cytometer (BD Bioscience). All data were processed by FlowJo (V10; Flowjo LLC, Ashland, Oreg.).

2.9. Transduction of the Retina in Rats

Adult male Sprague-Dawley rats were injected subretinally with 2.5 µl of the solution containing either the AAV2 control or the chemically modified vectors at a concentration of 1E12vg/mL. All animals were injected bilaterally, in one eye with the AAV2 control and the contralateral eye with the chemically modified AAV2+17 vector. Two groups of animals (n=8 per group) were used; one group injected AAV2 control vs AAV2+17 at 3e5Eq, and the second group with AAV2 control vs AAV2+17 at 3e6Eq. To follow the fluorescence due to GFP expression in the eye fundus, a non invasive imaging system was used at different time points; from 1 week post-injection up to 1.5 months post-injection.

2.10. Statistical Analysis

All the experiments are shown as mean±standard error (SEM). GraphPad Prism 5 software was used for statistical analysis. Data were subjected to one-way analysis of variance (ANOVA). Samples were considered significantly different if $*p<0.05$, $p<0.01$, $*p<0.001$.

2.11. Results and Conclusion

FIG. 1 represents covalent coupling of FITC on the capsid of AAV2 via primary amino groups.

(A) A dose of 1E12 vg of AAV2-GFP vectors were added to a solution of FITC (1E5 or 3E5 eq) in TBS buffer (pH 9.3) and incubated during 4h at RT. The solutions containing the vectors were dialyzed against dPBS+ 0.001% Pluronic to remove free FITC molecules that were non-binded to the AAV capsid.

(B) The same experimental procedure was followed but substituting FITC by fluorescein (3E5 eq), that do not contain the reactive residues (—N=C=S), in TBS pH 9.3 as control.

(C-E) AAV2 control and samples of AAV2 vectors incubated with FITC in TBS buffer (AAV2 FITC (1E5) and AAV2 FITC (3E5)) or incubated with fluorescein in TBS buffer (AAV2 Fluo (3E5)) were analyzed by fluorescence emission and dot blot. To this end, a total dose of 1E9 vg of each condition was loaded on a nitrocellulose membrane and analyzed by direct fluorescence emission (C), by dot blot using an anti-FITC antibody (D) or using the A20 antibody that recognize the entire capsid (E).

(F,G) A dose of 5E8 vg of the same samples was analyzed by Western blot using a polyclonal antibody to detect denaturated AAV capsid proteins (F) or using an anti-FITC antibody (G).

(H) A total dose of 1E10 vg of each condition was analyzed by silver nitrate staining. VP1, VP2 and VP3 are the three proteins constituting the AAV capsid. Protein size is indicated at the left of the images according to a protein ladder.

Figure 4:
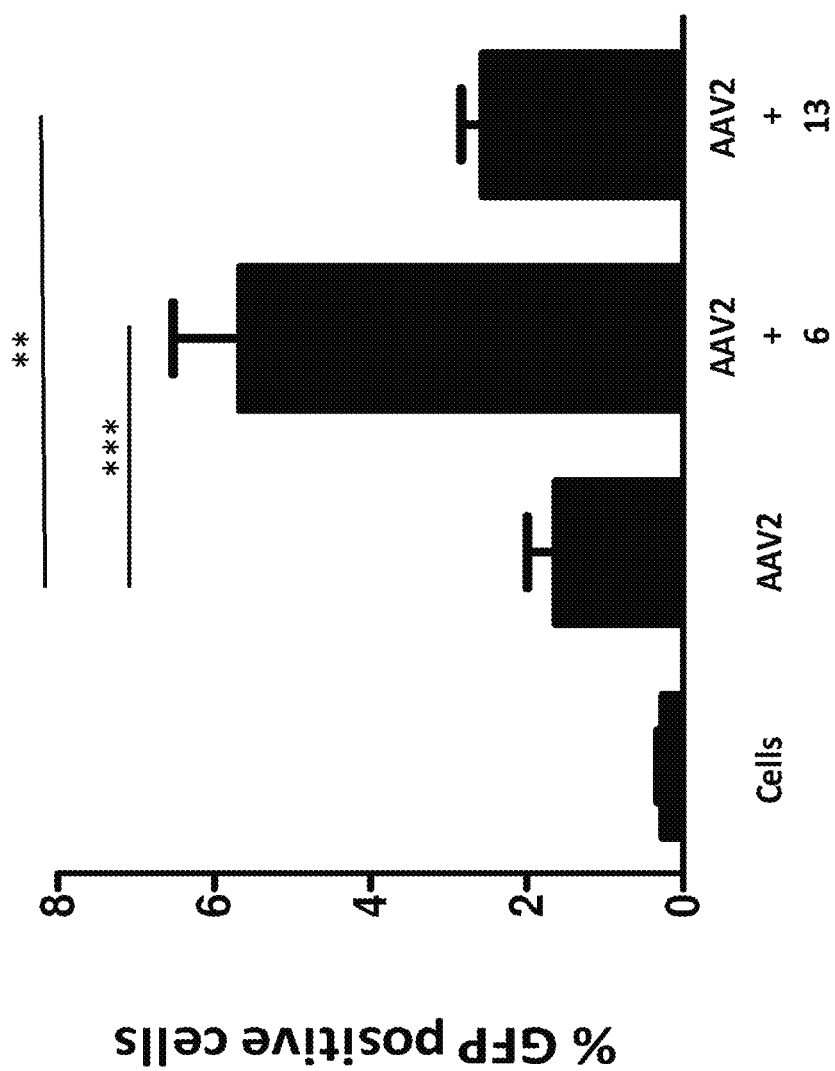
FIG. 4 illustrates the transduction of human primary hepatocytes with AAV2 and AAV2 vectors chemically modified with GalNAc ligands.

The proof of concept of the chemical modification of the capsid of AAV2 had been done by using the fluorophore FITC. To this end, two different quantities of FITC referring to 1E5 or 3E5 molar ratios against AAV2 were used (FIG. 4-A). The same molar ratios of fluorescein as control was also used (FIG. 4-B).

Positive A20 dot, for all the experimental conditions used, indicated that AAV2 capsids remain intact after undergoing the reaction with different molar ratios and subsequent dialysis against dPBS+pluronic (FIG. 4-C). Notably, positive FITC and negative fluorescein dots also demonstrated the covalent coupling of FITC on the virus capsids and not its adsorption (FIG. 4-D). The difference of intensity of the dot showed by fluorescence analyses on FIG. 4-E demonstrated that the covalent coupling of FITC is more efficient with 3E5 than 1E5 equivalents of FITC in these conditions.

Western blot analysis was performed to further confirm the impact of the molar ratio on the conjugation of FITC to the AAV capsid subunits. As before, the use of a Polyclonal antibody indicated that AAV2 capsid subunits remain intact with the molar ratios used (FIG. 4-F). As shown in FIG. 4-G, the capsid subunits from AAV2 and AAV2 incubated with fluorescein at the highest ratio did not yield any positive bands after incubation with the anti-FITC antibody. However, the use of this antibody clearly showed that the covalent coupling of FITC is more efficient with 3E5 than 1E5 equivalents of FITC in these conditions (FIG. 4-G).

In order to visualize all the proteins and to confirm that there is no degradation during the chemical process, a silver staining of the different conditions was also performed.

As shown in FIG. 4-H, it can be observed in all the conditions tested a more intense VP3 band as compared to VP1 and VP2. It also indicated that AAV2 capsid subunits remain intact after undergoing the reaction and subsequent dialysis against dPBS+pluronic.

Figure 2:
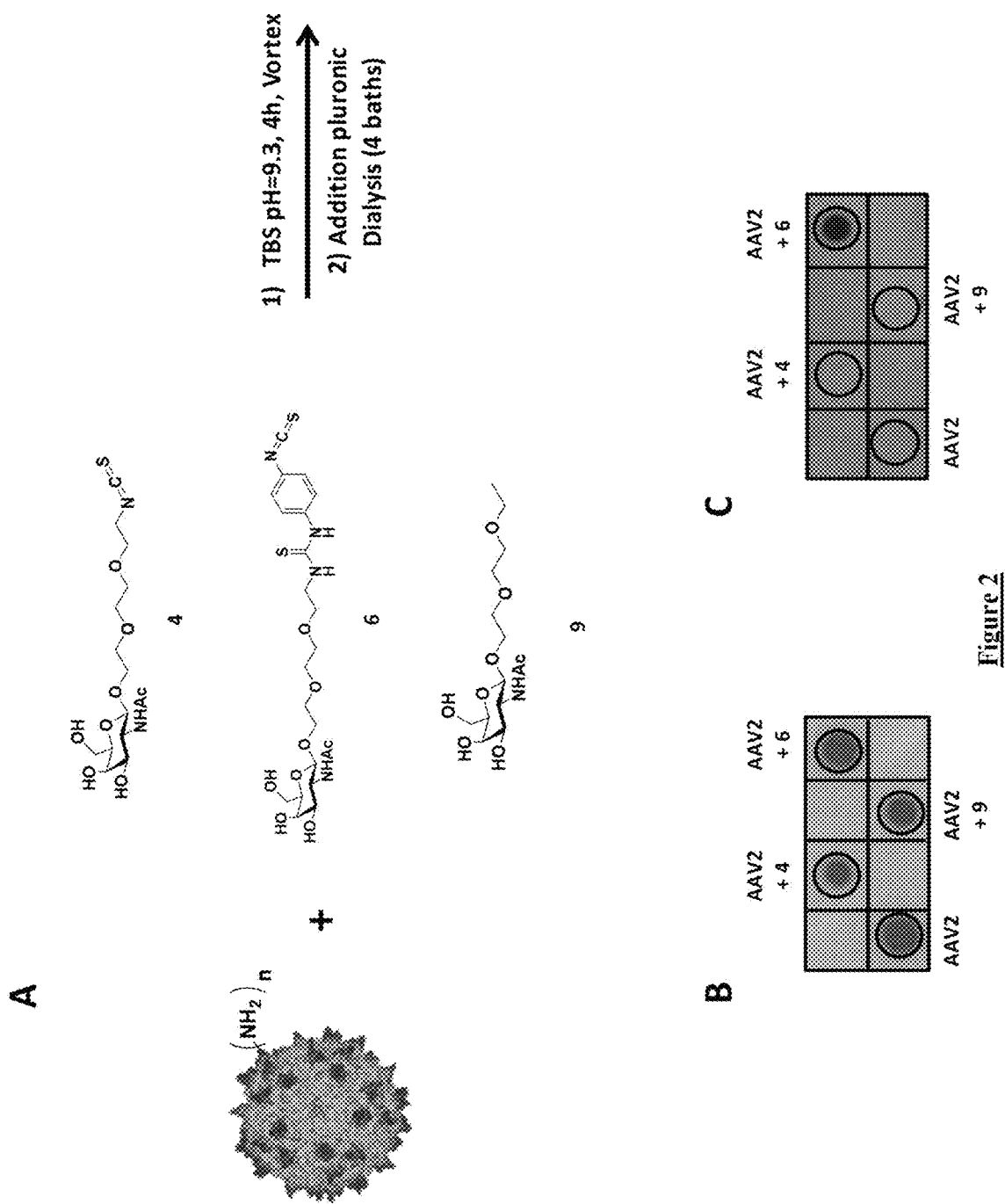
FIG. 2 illustrates the identification of the reactive function for the covalent coupling of GalNAc ligands on the capsid of AAV2 via primary amino groups.

FIG. 2 represents an identification of the reactive function for the covalent coupling of GalNAc ligands on the capsid of AAV2 via primary amino groups.

(A) A dose of 1E12 vg of AAV2-GFP vectors were added to a solution of compound 4 (containing a GalNAc ligand with a —N=C=S reactive function) or compound 6 (containing a GalNAc ligand with an Aryl-N=C=S reactive function) (3E5 eq) in TBS buffer (pH 9.3) and incubated during 4h at RT. After the incubation, vectors were dialyzed against dPBS+ 0.001% Pluronic to remove free GalNAc ligands molecules that were non-binded to the AAV capsid. The same experimental procedure was followed with compound 9 (3E5 eq), that do not contain the reactive residues (—N=C=S), in TBS pH 9.3 as control.

(B,C) AAV2 control and samples of AAV2 vectors incubated with GalNAc ligands in TBS buffer (AAV2+4, AAV2+6 and AAV2+9) were analyzed by dot blot. To this end, a total dose of 1E10 vg of each conditions was loaded on a nitrocellulose membrane and labeled using the A20 antibody that recognize the entire capsid (B) or using the soybean-FITC lectin that recognizes N-acetylgalactosamine sugar (C).

In order to determine the optimal coupling function on ligand for the anchor on the surface of the capsid of AAV2, 3 compounds were synthetized having a —NCS (4) or an aryl-NCS (6) (like for FITC) and another (9) without any reactive function to ensure the covalent coupling of these hepatic ligands and not their adsorption on the surface of the capsid (FIG. 2-A).

For the validation of the covalent coupling of these hepatic ligands on AAV2 dot blot techniques was used. Positive A20 dot, for all the experimental conditions used, indicated that AAV2 capsids remain intact after undergoing the reaction and subsequent dialysis against dPBS+pluronic (FIG. 2-B). Positive Soybean Lectin dot (known to interact with GalNAc residue) detected with the compound 6 demonstrated that in these conditions the aryl-NCS is the only coupling function that reacted with the amino group on the capsid of AAV2. As observed with fluorescence, no detection was observed with compound 9 therefore validating the covalent coupling and not the adsorption of compound 6 on the surface of the capsid of AAV2 (FIG. 2-C).

The combined use of TBS buffer and ligand having an aryl-NCS function allow the covalent coupling of different molecule on the surface of AAV2 in conditions that have no adverse effect on the vector.

Figure 3:
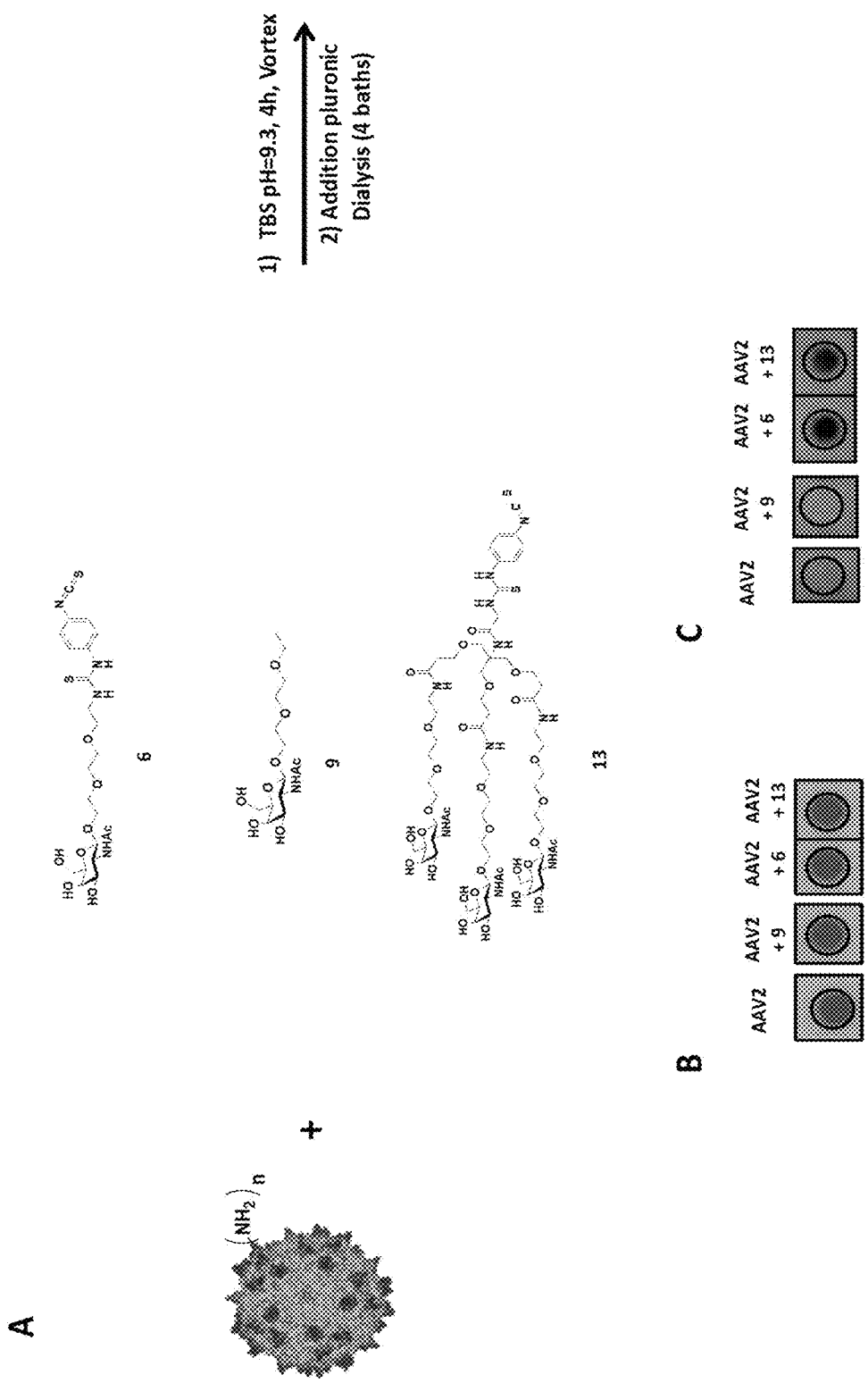
FIG. 3 illustrates the covalent coupling of GalNAc ligands on the capsid of AAV2 via primary amino groups.

FIG. 3 represents covalent coupling of GalNAc ligands on the capsid of AAV2 via primary amino groups.
 (A) A dose of 1E12 vg of AAV2-GFP vectors were added to a solution of compound 6 (a GalNAc monomer ligand with a Aryl-N=C=S reactive function) or compound 13 (a GalNAc trimer ligand with a Aryl-N=C=S reactive function) (3E5 eq) in TBS buffer (both at pH 9.3) and incubated during 4h at RT. After the incubation, vectors were dialyzed against dPBS+ 0.001% Pluronic to remove free GalNAc ligands molecules that were non-binded to the AAV capsid. The same experimental procedure was followed with compound 9 (3E5 eq), that do not contain the reactive residues (Aryl-N=C=S), in TBS pH 9.3 as control.
 (B,C) AAV2 control and samples of AAV2 vectors incubated with GalNAc ligands in TBS buffer (AAV2+6, AAV2+9 and AAV2+13) were analyzed by dot blot. To this end, a total dose of 1E10 vg of each conditions was loaded on a nitrocellulose membrane and labeled using the A20 antibody that recognize the entire assembled capsid (B) or using the soybean-FITC lectin that recognizes N-acetylgalactosamine sugar (C).
 (D,E) AAV2 control and samples of AAV2 vectors incubated with GalNAc ligands in TBS buffer (AAV2+6, AAV2+9 and AAV2+13) were analyzed by western blot. A total dose of 1E10 vg of each conditions was loaded on a nitrocellulose membrane and labeled by a polyclonal antibody to detect denaturated AAV capsid proteins (D) or using the soybean-FITC lectin (E). VP1, VP2 and VP3 are the three proteins constituting the AAV capsid. Protein size is indicated at the left of the images according to a protein ladder.

After the validation of the chemical coupling of 6 and its aryl-NCS function, a trimer GalNAc, i.e compound 13, compound having the same anchor function, was also tested. This specific trimer had been described to improve the interaction with the ASPGr on the surface of hepatocytes (FIG. 3-A).

For the validation of the covalent coupling of these hepatic ligands on AAV2 dot and western blot techniques were used. Positive A20 dot, for all the experimental conditions used, indicated that AAV2 capsids remain intact after undergoing the reaction and subsequent dialysis against dPBS+pluronic (FIG. 3-B). Positive Soybean Lectin dot (known to interact with GalNAc residue) detected with the compounds 6 and 13. As observed with fluorescein, no detection was observed with compound 9 therefore validating the covalent coupling and not the adsorption of 6 and 13 on the surface of the capsid of AAV2 (FIG. 3-C).

Western blot analysis was performed to confirm the conjugation of 6 and 13 on the primary amino group on the AAV2 capsid subunits. The use of a Polyclonal antibody indicated that AAV2 capsid subunits remain intact with the different ligands used on this coupling step (FIG. 3-D). As shown in FIG. 3-E, the capsid subunits from AAV2 and AAV2 incubated with 9 did not yield any positive bands after incubation with the specific Soybean Lectin. However, the use of this lectin with compounds 6 and 13 clearly showed positive bands at the correct molecular weights of VP1, VP2, and VP3, demonstrating the covalent coupling of these GalNAc ligands on the three subunits of the AAV capsid.

FIG. 4 represents the transduction of human primary hepatocytes with AAV2 and AAV2 vectors chemically modified with GalNAc ligands. Human primary hepatocytes (2E5 cell/well) were incubated in P24 plates and were transduced with AAV2 control (immediately upon thawing), GalNAc-AAV2 (AAV2+6, AAV2+13) at a MOI of 1E5. All AAV vectors encoded for GFP. The percentage of GFP positive cells have been measured by FACS analysis 48h after the transduction. Non transduced cells (cells) were used as a control for fluorescence background. Four replicates of each condition have been analyzed by ANOVA test (* $p<0.001$,  $p<0.01$). Data are represented as mean±SD.

In order to evaluate the efficiency of the chemical modification with hepatic ligand on AAV2, the transduction of these modified or non-modified particles on human primary hepatocytes was evaluated. As shown in FIG. 4, the chemical modification of the capsid of AAV2 with the compound 6 increased the percentage of GFP positive cells by a factor 4 which is statistically significant in comparison with AAV2 which followed the same experimental procedure. The chemical coupling of 13 did not resulted in the same increasing of the percentage of GFP positive cells but this increasing is statistically significant.

Figure 5:
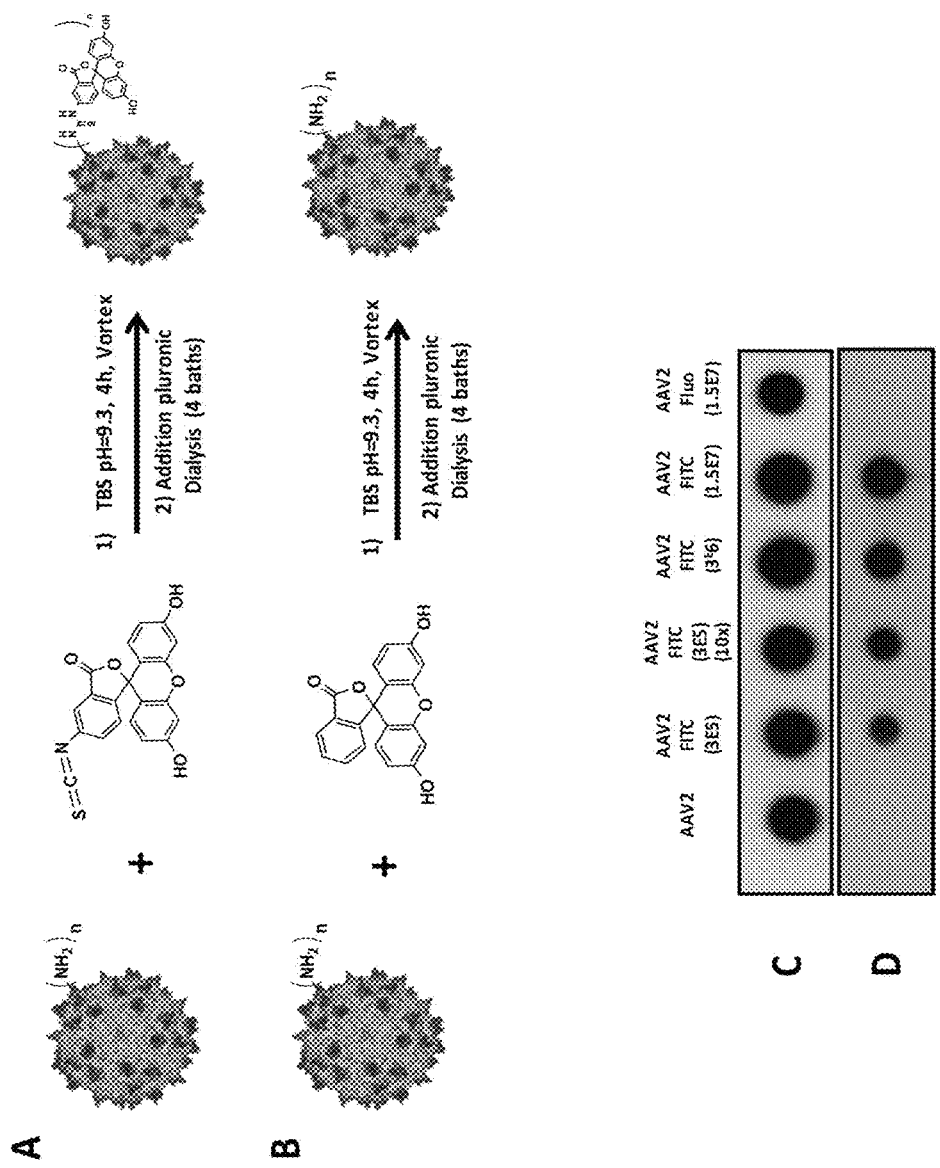
FIG. 5 illustrates the effect of the number of equivalents of ligands on the efficacy of coupling via primary amino group (Example with FITC).

FIG. 5 represents the effect of the number of equivalents of ligands on the efficacy of coupling via primary amino group (Example with FITC).
 (A) A dose of 1E12 vg of AAV2-GFP vectors was added to a solution of FITC (3E5 eq, 3E5 eq-10x (3E5 eq but with the volume of the reaction reduced 1/10), 3E6 eq, 1.5E7 eq) in TBS buffer at pH 9.3 and incubated during 4h at RT. The solutions containing the vectors were dialyzed against dPBS+0.001% Pluronic to remove free FITC molecules that were non-binded to the AAV capsid.
 (B) The same experimental procedure was followed but substituting FITC by fluorescein (1.5E7 eq), that do not contain the reactive residues (N=C=S), in TBS pH 9.3 as control. (C,D) AAV2 control and samples of AAV2 vectors incubated with FITC in TBS buffer (AAV2 FITC (3E5), AAV2 FITC (3E5-10x), AAV2 FITC (3E6) and AAV2 FITC (1.5E7)) or incubated with fluorescein in TBS buffer (AAV2 Fluo (1.5E7)) were analyzed by dot blot. A total dose of 1E9 vg of each conditions was loaded on a nitrocellulose membrane and labeled by the A20 antibody that recognize the entire capsid (C) or using an anti-FITC antibody (D).
 (E,F) A dose of 5E8 vg of the same samples was analyzed by Western blot using a polyclonal antibody to detect denaturated AAV capsid proteins (E) or using an anti-FITC antibody (F). VP1, VP2 and VP3 are the three proteins constituting the AAV capsid. Protein size is indicated at the left of the images according to a protein ladder.
 (G) HeLa cells (2E5 cell/well) were incubated in cell stacks and were transduced with AAV2 FITC (3E5), AAV2 FITC (3E6) and AAV2 FITC (1.5E7)) at a MOI of 1E5. All AAV vectors encoded for GFP. Confocal microscopy analyses were done after 4h of transduction, to avoid the expression of the GFP, by visualization of the green FITC fluorescence and red fluorescence A20 immunolabeling (A20 primary antibody and A1647 secondary antibody).

To modulate the number of ligand on the AAV2 the molar ratio of FITC used on the TBS buffer was increased and evaluated if it had an influence on the number of molecule coupled on the surface of the capsid of AAV2. To saturate the capsid of AAV2 with FITC, this ratio was increased from 3E5 to 1.5E7.

Dot and western blot analysis was performed to further confirm the impact of the molar ratio on the conjugation of FITC to the AAV capsid subunits. As before, the use of A20 and a Polyclonal antibody indicated that AAV2 capsid subunits remain intact with the different molar ratios used (FIG. 5-C,E). As shown in FIG. 5-D,F, the capsid subunits from AAV2 and AAV2 incubated with fluorescein at the highest ratio did not yield any dot or positive bands after incubation with the anti-FITC antibody. However, the use of this antibody clearly showed that the covalent coupling of FITC is more efficient when its molar ratio increased (FIG. 5-F). It is also important to note that doing the coupling with 3E5 molar ratio of FITC in 10x TBS buffer allowed the coupling of a more important number of this fluorophore on the capsid of this vector.

For AAV2-FITC (3E5), green FITC fluorescence (J) and red fluorescence A20 immunolabeling (K) were detected, colocalisation of FITC and A20-A1647 was observed in yellow by merging images obtained in green and red channels (L) demonstrating the covalent coupling of FITC on the capsid of AAV2. On the contrary, AAV2-FITC (3E6) and AAV2-FITC (1.5E7) samples (S,V) were not recognized by A20 immunolabeling (K) and, thus, colocalisation of FITC and A20-A1647 was not observed (T,U,W,X). These results suggested that increased number of FITC ligands on the surface of the capsid of AAV2 could reduce the interaction with A20 antibodies and suggest the possibility that modified capsids have less interactions with surface recognition antibodies in general.

Figure 6:
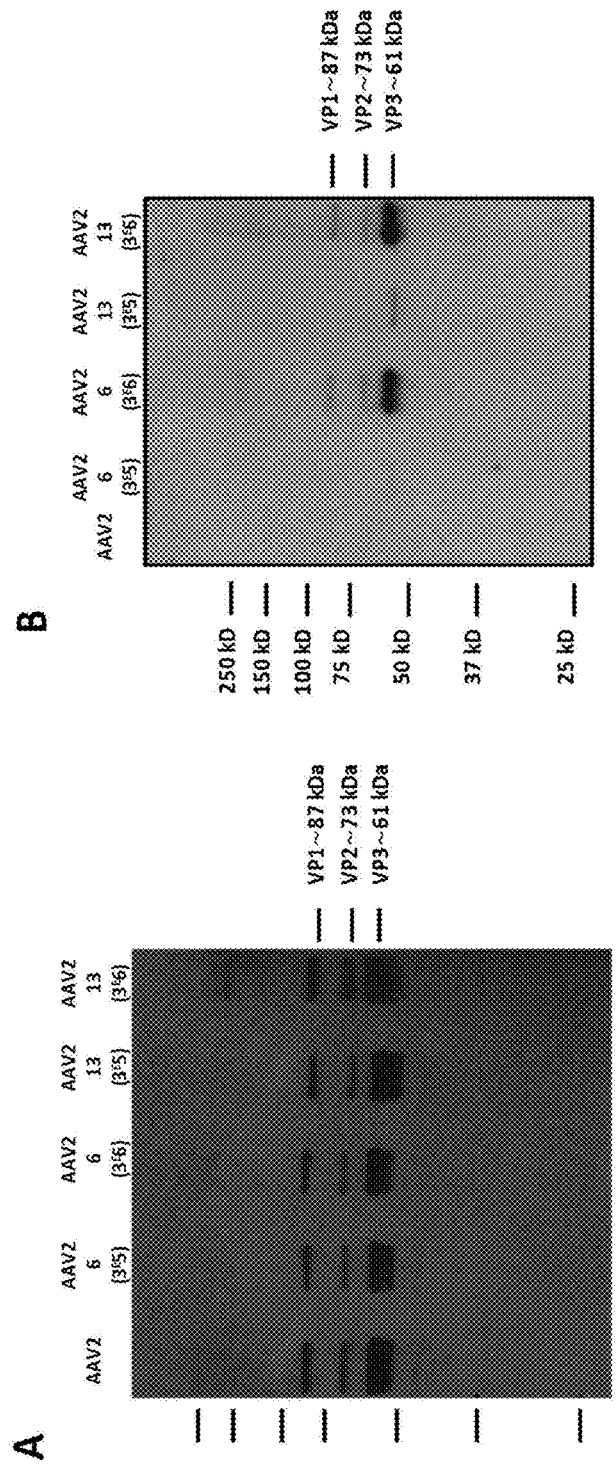
FIG. 6 illustrates the effect of the number of equivalents of GalNAc ligands on the efficacy of coupling via primary amino group (Example with 6 and 13) and the transduction of murine primary hepatocytes.

FIG. 6 represents the effect of the number of equivalents of GalNAc ligands on the efficacy of coupling via primary amino group (Example with 6 and 13) and the transduction of murine primary hepatocytes.

(A, B) A dose of 1E12 vg of AAV2-GFP vectors was added to a solution of 6 and 13 (3E5 and 3E6 eq) in TBS buffer at pH 9.3 and incubated during 4h at RT. The solutions containing the vectors were dialyzed against dPBS+0.001% Pluronic to remove free GalNAc ligands molecules that were non-binded to the AAV capsid.

AAV2 control and samples of AAV2 vectors incubated with GalNAc ligands in TBS buffer were analyzed by western blot. A total dose of 1E10 vg of each conditions was loaded on a nitrocellulose membrane and labeled by a polyclonal antibody to detect denaturated AAV capsid proteins (A) or using the soybean-FITC lectin (B). VP1, VP2 and VP3 are the three proteins of the AAV capsid. Protein size is indicated at the left of the images according to a protein ladder.

(C) transduction of murine primary hepatocytes with AAV2 and AAV2 vectors chemically modified with GalNAc ligands. Murine primary hepatocytes (2E5 cell/well) were incubated in P24 plates and were transduced with AAV2 control (immediately upon thawing), GalNAc-AAV2 (AAV2+6 (3E5 and 3E6 eq)) at a MOI of 1E5. All AAV vectors encoded for GFP under the control of CAG promoter. The percentage of GFP positive cells was measured by FACS analysis 72h post-transduction. Non transduced cells (cells) were used as a control (i.e. fluorescence background). Three replicates of each condition have been analyzed by ANOVA test (* $p<0.001$,  $p<0.01$). Data are represented as mean±SD.

To modulate the number of ligand on the AAV2, the molar ratio of 6 and 13 used on the TBS buffer was increased and evaluated if it had an influence on the number of molecule coupled on the surface of the capsid of AAV2. To saturate the capsid of AAV2 with 6 and 13, this ratio was increased from 3E5 to 3E6 equivalent (Eq).

Western blot analysis was performed to further confirm the impact of the molar ratio on the conjugation of 6 and 13 to the AAV capsid subunits. As shown before, the use of a polyclonal antibody (against capsid) indicated that AAV2 capsid subunits remain intact with the different molar ratios used (FIG. 6-A). As shown in FIG. 6-B, the use of the Soybean lectin clearly showed that the covalent coupling of 6 and 13 was more efficient when the molar ratio increased from 3E5 to 3E6. In order to evaluate the efficiency of the chemical modification with the hepatic ligand on AAV2, the transduction of these modified or non-modified AAV2 particles on murine primary hepatocytes was evaluated. As shown in FIG. 6-C, the chemical modification of the capsid of AAV2 with the compound 6 at two doses (3E5 and 3E6 eq) increased the percentage of GFP positive cells by a factor of 2 (3E5) and 6 (3E6) which is statistically significant in comparison with AAV2 control vector.

Figure 7:
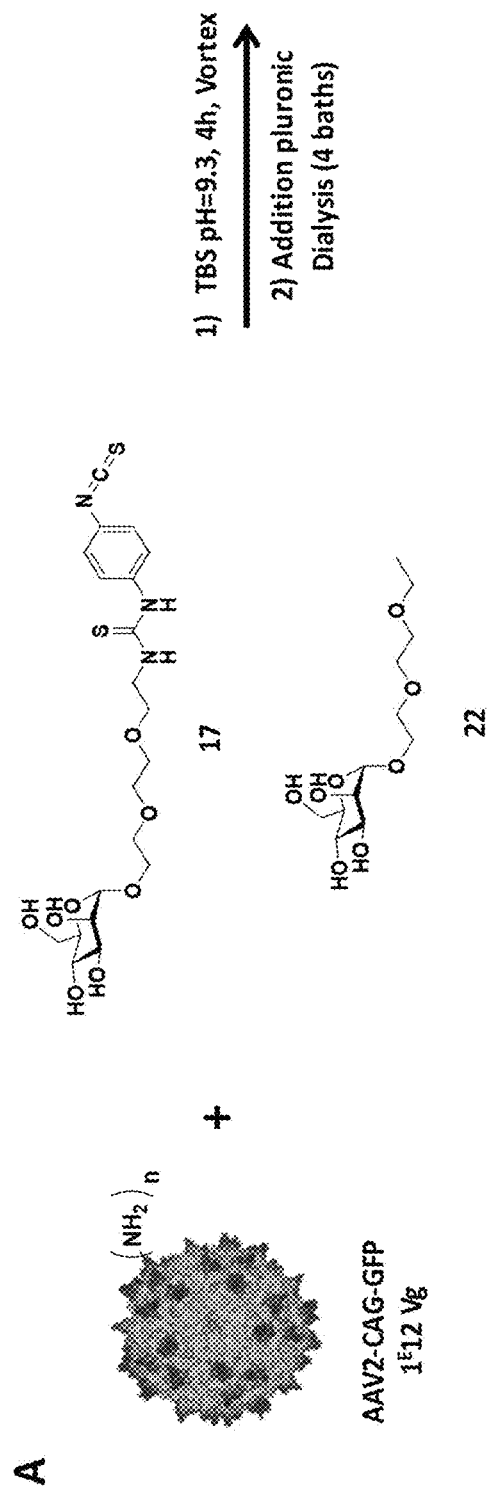
FIG. 7 illustrates the effect of the number of equivalents of Mannose ligands on the efficacy of coupling via primary amino group (Example with 6 and 13) and the transduction of the retina in rats.

FIG. 7. Effect of the number of equivalents of Mannose ligands on the efficacy of coupling via primary amino group (Example with 17) and the transduction of the retina in rats.

(A) A dose of 1E12 vg of AAV2-GFP vectors were added to a solution of compound 17 (a mannose monomer ligand with a Aryl-N=C=S reactive function) (3E5 and 3E6 eq) in TBS buffer (both at pH 9.3) and incubated during 4h at RT. After the incubation, vectors were dialyzed against dPBS+0.001% Pluronic to remove free mannose ligands molecules that were non-binded to the AAV capsid. The same experimental procedure was followed with compound 22 (3E6 eq), that do not contain the reactive residues (Aryl-N=C=S), in TBS pH 9.3 as control.

(B, C) AAV2 control and samples of AAV2 vectors incubated with mannose ligands in TBS buffer were analyzed by western blot. A total dose of 1E10 vg of each conditions was loaded on a nitrocellulose membrane and labeled by a polyclonal antibody to detect denaturated AAV capsid proteins (B) or using the Concanavalin A lectin that recognize specifically the mannose group (C). VP1, VP2 and VP3 are the three proteins constituting the AAV capsid. Protein size is indicated at the left of the images according to a protein ladder.

(D) Direct visualization of GFP fluorescence in the eye fundus of rats injected subretinally with AAV2 control (AAV2) or with AAV2 incubated with mannose ligand (compound 17) at two different doses (3e5Eq and 3e6Eq). Images were taken at different time points; from 1 week post-injection up to 1.5 months post-injection using non invasive techniques.

To modulate the number of mannose ligand on the AAV2 surface the molar ratio of 17 used on the TBS buffer was increased and evaluated if it had an influence, as GalNAc ligands, on the number of molecule coupled on the surface of the capsid of AAV2. To saturate the capsid of AAV2 with 17 this ratio was increased from 3E5 to 3E6.

Western blot analysis was performed to further confirm the impact of the molar ratio on the conjugation of 17 to the AAV capsid subunits. As before, the use of a Polyclonal antibody indicated that AAV2 capsid subunits remain intact with the different molar ratios used (FIG. 7-B). As shown in FIG. 7-C, the use of the Concanavalin A lectin clearly showed that the covalent coupling of 17 is more efficient when the molar ratio increased from 3E5 to 3E6.

Non invasive eye funduscopy showed GFP expression in the retina of both AAV2 control and AAV2+17 treated eyes during the whole study (FIG. 7D). Images on the left are representative of the eyes treated with AAV2+17 at a dose of 3e5Eq and the intensity of the fluorescence was similar compare to AAV2 control (contralateral eyes). However, on the right images it could be observed that the eyes treated with AAV2+17 at a dose of 3e6Eq had a broaden and brighter GFP intensity at all time points compare to control AAV2 treated contralateral eyes. It may be noticed that pictures taken at 3 weeks, 1 month and 1.5 months from the eyes treated with AAV2+17 at the dose 3e6Eq were adjusted to avoid saturation of the signal because the fluorescence signal was much higher than contralateral eyes.

Figure 8:
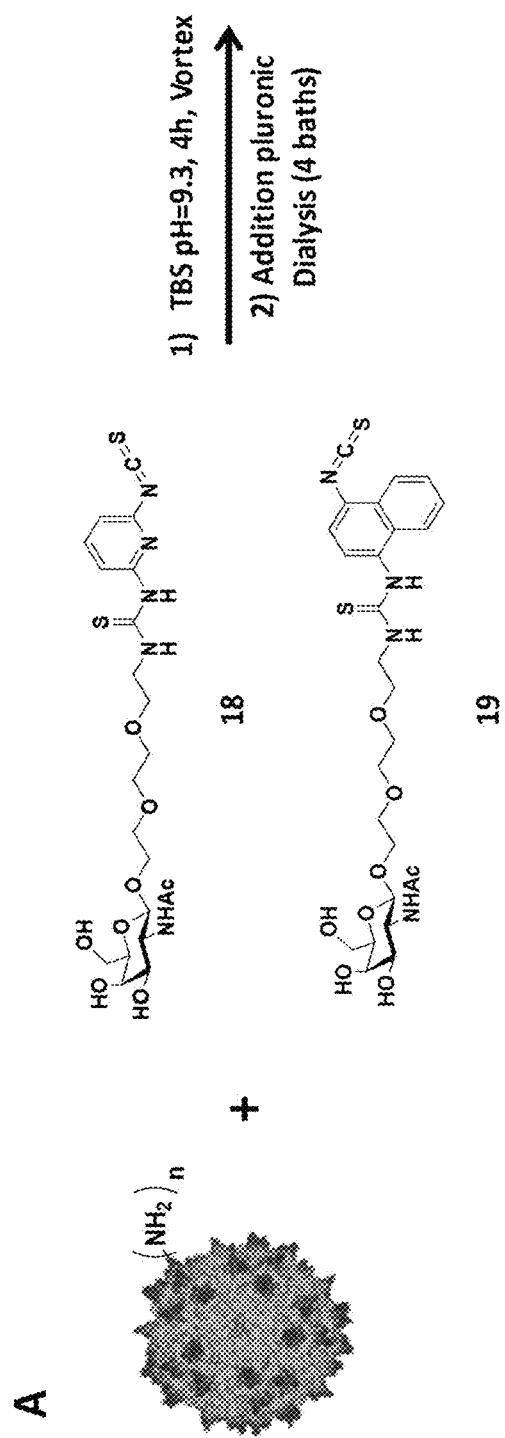
FIG. 8 illustrates the identification of ligands 18 and 19 with different reactive function for the covalent coupling of GalNAc ligands on the capsid of AAV2 via primary amino groups.

FIG. 8. Identification of different reactive function for the covalent coupling of GalNAc ligands on the capsid of AAV2 via primary amino groups.

(A) A dose of 1E12 vg of AAV2-GFP vectors were added to a solution of compound 18 or 19 (3E6 eq) in TBS buffer (pH 9.3) and incubated during 4h at RT. After the incubation, vectors were dialyzed against dPBS+ 0.001% Pluronic to remove free GalNAc ligands that were non-binded to the AAV capsid.

(B,C) A dose of 1E10 vg of each samples was analyzed by Western blot using a polyclonal antibody to detect denaturated AAV capsid proteins (B) or using the soybean lectin (C).

In order to determine different coupling function on ligand to allow proper anchoring on the surface of the capsid of AAV, two compounds, 18 (pyridine isothiocyanate derivative) and 19 (naphthalene isothiocyanate derivative), were synthetized (FIG. 8-A).

Western blot analysis was performed to confirm the conjugation of 18 and 19 on the primary amino group on the AAV2 capsid subunits. The use of a Polyclonal antibody indicated that AAV2 capsid subunits remain intact with the different ligands used on this coupling step (FIG. 8-B). The use of the soybean lectin (that recognize the GalNAc group) with compounds 18 and 19 showed positive bands at the correct molecular weights of VP1, VP2, and VP3, demonstrating the covalent coupling of these GalNAc ligands on the three subunits of the AAV capsid.

The combined use of TBS buffer and ligand having an aryl-NCS, polyaryl-NCS and heteroaryl-NCS function allow the covalent coupling of different molecules on the surface of AAV2 in conditions that have no adverse effect on the vector.

Figure 9:
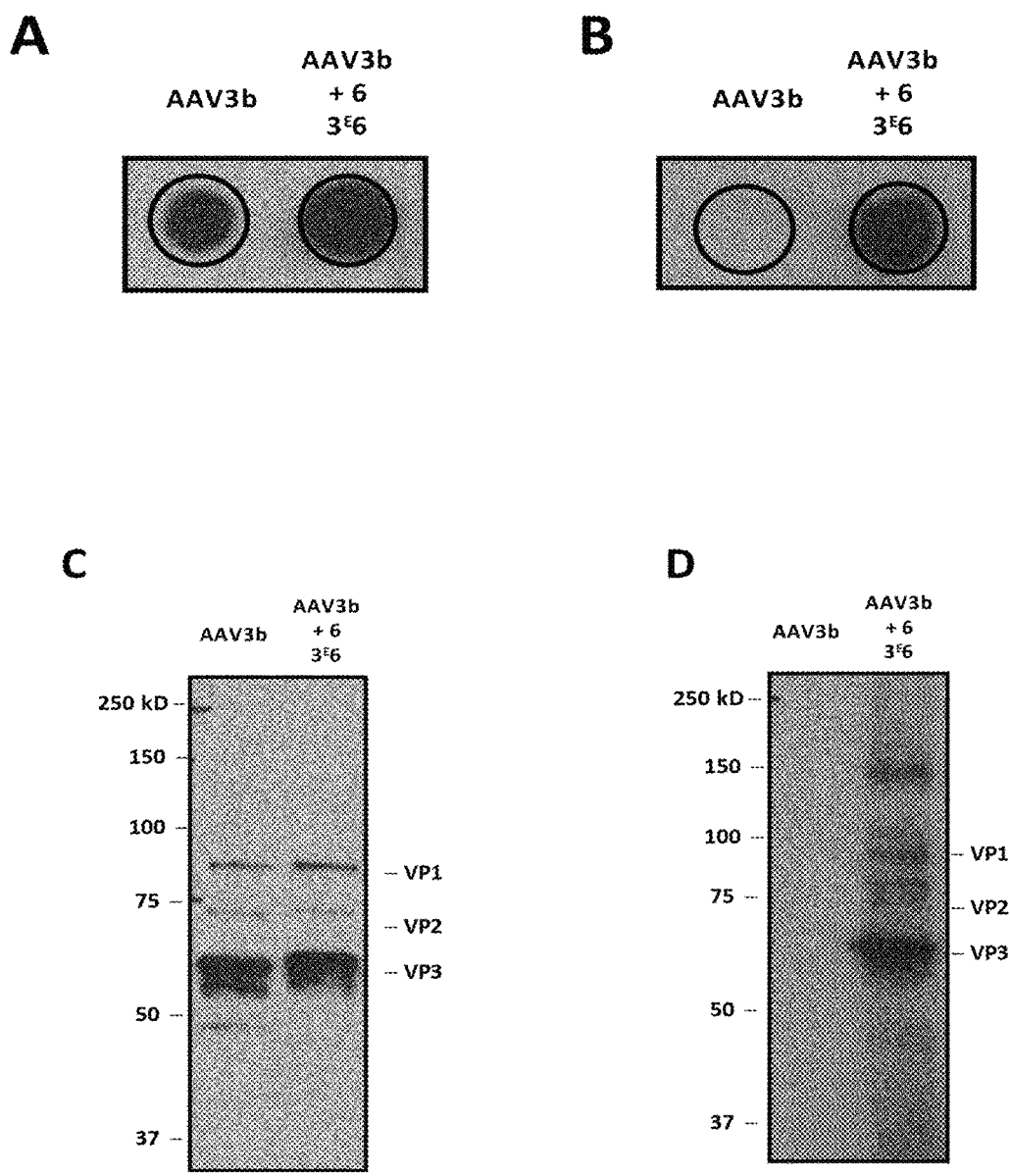
FIG. 9 illustrates the covalent coupling of 6 on the capsid of AAV3b via primary amino groups.

FIG. 9 represents covalent coupling of 6 on the capsid of AAV3b via primary amino groups.

A dose of 1E12 vg of AAV3b-GFP vectors were added to a solution of 6 (3E6 eq) in TBS buffer (pH 9.3) and incubated during 4h at RT. The solutions containing the vectors were dialyzed against dPBS+0.001% Pluronic to remove free 6 molecules that were non-binded to the AAV capsid.

(A,B) A total dose of 1E9 vg of each condition was loaded on a nitrocellulose membrane and analysed by dot blot using the A20 antibody that recognize the assembled capsid (A) an the soybean lectin (B).

(C,D) A dose of 1E10 vg of the same samples was analyzed by Western blot using a polyclonal antibody to detect denaturated AAV capsid proteins (C) or using the soybean lectin (D).

The proof of concept of the chemical modification of the capsid of AAV3b was done by using the compound 6 as for AAV2. To this end, 3E6 molar ratios of 6 against AAV3b were used.

Positive A20 dot, for all the experimental conditions used, indicated that AAV3b capsids remain intact after the chemical reaction (FIG. 9-A). Notably, positive dots with soybean lectine also demonstrated the covalent coupling of 6 on the AAV capsids (FIG. 9-B).

Western blot analysis was performed to further confirm the coupling of 6 to the AAV3b capsid subunits. As shown before, the use of a polyclonal antibody indicated that AAV3b capsid subunits remained intact (FIG. 9-C). As shown in FIG. 9-D, the use of the soybean lectin showed the covalent coupling of 6 on those AAV capsid subunits.

Conclusion

The experimental conditions used for the coupling clearly showed that it is possible to modulate the coupling of a ligand on the surface of the capsid of AAV2 and AAV3b. New—AAV-derived vectors are thus available by chemically coupling ligands of any nature on the capsid surface. Specific activity and therapeutic index of the vectors may also be improved by this method.

The invention claimed is:

1. A method of delivering a nucleic acid to a cell, the method comprising contacting a cell with an AAV vector particle comprising a ligand covalently linked to a primary amino group of an AAV capsid polypeptide via a -CSNH- bond and a nucleic acid to be expressed in the contacted cell.

2. The method of claim 1, wherein the contacting is in vivo.

3. The method of claim 2, wherein the contacting comprises systemic administration.

4. The method of claim 1, wherein the ligand comprises a mannose, galactose or N-acetylgalactosamine moiety. and the particle targets a cell in the central nervous system.

5. The method of claim 1 wherein the ligand comprises a mono- or polysaccharide moiety.

6. The method of claim 5, wherein the ligand comprises a mannose, galactose or N-acetylgalactosamine moiety.

7. The method of claim 1 wherein the contacting comprises intrathecal, intracranial, intracerebral, or retinal administration.

8. The method of claim 1, wherein the ligand comprises a mannose, galactose or N-acetylgalactosamine moiety, and the particle targets a cell in the eye.

9. The method of claim 1 wherein the contacting comprises contacting a cell of an eye or a conjunctival administration.

* * * * *

SEQUENCE LISTING

```
<160> NUMBER OF SEQ ID NOS: 5

<210> SEQ ID NO 1
<211> LENGTH: 7
<212> TYPE: PRT
<213> ORGANISM: Artificial Sequence
<220> FEATURE:
<223> OTHER INFORMATION: muscle targeting peptide (MTP)

<400> SEQUENCE: 1

Ala Ser Ser Leu Asn Ile Ala
1               5

<210> SEQ ID NO 2
<211> LENGTH: 7
<212> TYPE: PRT
<213> ORGANISM: Artificial Sequence
<220> FEATURE:
<223> OTHER INFORMATION: muscle targeting peptide (MTP)

<400> SEQUENCE: 2
```

```
Trp Asp Ala Asn Gly Lys Thr
1               5

<210> SEQ ID NO 3
<211> LENGTH: 7
<212> TYPE: PRT
<213> ORGANISM: Artificial Sequence
<220> FEATURE:
<223> OTHER INFORMATION: muscle targeting peptide (MTP)

<400> SEQUENCE: 3

Gly Glu Thr Arg Ala Pro Leu
1               5

<210> SEQ ID NO 4
<211> LENGTH: 9
<212> TYPE: PRT
<213> ORGANISM: Artificial Sequence
<220> FEATURE:
<223> OTHER INFORMATION: muscle targeting peptide (MTP)

<400> SEQUENCE: 4

Cys Gly His His Pro Val Tyr Ala Cys
1               5

<210> SEQ ID NO 5
<211> LENGTH: 7
<212> TYPE: PRT
<213> ORGANISM: Artificial Sequence
<220> FEATURE:
<223> OTHER INFORMATION: muscle targeting peptide (MTP)

<400> SEQUENCE: 5

His Ala Ile Tyr Pro Arg His
1               5
```